United States Patent [19]

Cargill et al.

[11] Patent Number: 5,691,817
[45] Date of Patent: Nov. 25, 1997

[54] APPARATUS AND METHOD FOR CALIBRATION IN A SPECTROPHOTOMETER

[75] Inventors: Mark A. Cargill, Belding; Bernard J. Berg, Kentwood, both of Mich.

[73] Assignee: X-Rite, Incorporated, Grandville, Mich.

[21] Appl. No.: 700,155

[22] Filed: Aug. 20, 1996

Related U.S. Application Data

[63] Continuation of Ser. No. 514,792, Aug. 14, 1995, abandoned, which is a continuation of Ser. No. 975,981, Nov. 13, 1992, abandoned, which is a continuation of Ser. No. 679,995, Mar. 29, 1991, abandoned, which is a continuation of Ser. No. 487,670, Mar. 1, 1990, abandoned.

[51] Int. Cl.$^6$ .................................................. G01N 21/25
[52] U.S. Cl. .................................................. 356/405
[58] Field of Search .................................... 356/405, 416, 356/407, 418, 300, 319; 250/252.1 A

[56] References Cited

U.S. PATENT DOCUMENTS

| | | |
|---|---|---|
| 2,287,322 | 6/1942 | Nelson . |
| 3,244,062 | 4/1966 | Sweet . |
| 3,322,025 | 5/1967 | Dauser . |
| 3,614,241 | 10/1971 | Acton et al. . |
| 4,003,660 | 1/1977 | Christie, Jr. et al. . |
| 4,055,813 | 10/1977 | French .................... 330/363 |
| 4,125,329 | 11/1978 | French et al. ............ 356/405 |
| 4,194,838 | 3/1980 | Bey et al. ................. 356/404 |
| 4,239,393 | 12/1980 | Tobias ...................... 356/407 |
| 4,350,441 | 9/1982 | Wicnienski ............... 356/40 |
| 4,417,818 | 11/1983 | Weisner .................... 356/404 |
| 4,444,505 | 4/1984 | Imamoto et al. ......... 356/380 |
| 4,624,571 | 11/1986 | Salda et al. ............... 356/406 |
| 4,654,794 | 3/1987 | O'Brien .................... 364/413 |
| 4,681,455 | 7/1987 | Jeschke et al. ........... 356/445 |
| 4,750,838 | 6/1988 | De Wolf et al. ......... 356/445 |
| 4,773,761 | 9/1988 | Sugiyama et al. ........ 356/405 |
| 4,780,744 | 10/1988 | Porter et al. .............. 364/526 |
| 4,788,650 | 11/1988 | Willis et al. .............. 364/526 |
| 4,814,597 | 3/1989 | Kruger et al. ............ 250/205 |
| 4,917,495 | 4/1990 | Steenhoek ................. 356/405 |
| 4,989,982 | 2/1991 | Osaki et al. .............. 356/405 |
| 5,004,349 | 4/1991 | Sato et al. ................ 356/402 |

Primary Examiner—K. Hantis
Attorney, Agent, or Firm—Varnum, Riddering, Schmidt & Howlett LLP

[57] ABSTRACT

A spectrophotometer apparatus (200) is adapted to provide spectral reflectance measurements of object samples. The apparatus (200) comprises a source light (254) and a reflection optics assembly (264, 268). Signals representative of reflected light are analyzed and data provided to an operator representative of the spectral response characteristics of the object sample (252). The apparatus (200) further comprises a side sensor (276) having a fixed spectral response characteristic for compensating the reflectance measurements in accordance with the light intensity emanating from the lamp. For purposes of calibration, a series of time-sequenced measurements are made of a reference sample. Utilizing these measurements, the apparatus (200) provides computations of compensation coefficients for each spectral segment. The compensation coefficients are utilized, with the side sensor measurements, to provide normalization of the reflectance measurements for each segment and for each measurement within the timed sequence. For each segment, a scale factor is then determined. The scale factors, compensation coefficients and side sensor measurements are employed to compensate actual reflectance measurements, with further compensation provided by a determination of temperature coefficients.

43 Claims, 9 Drawing Sheets

APPARATUS AND METHOD FOR CALIBRATION IN A SPECTROPHOTOMETER

This application is a continuation of Ser. No. 08/514,792 filed Aug. 14, 1995 which is a continuation of Ser. No. 07/975,981 filed Nov. 13, 1992 which is a continuation of Ser. No. 07/679,995 filed Mar. 29, 1991 which is a continuation of Ser. No. 07/487,670 filed Mar. 1, 1990, all now abandoned.

BACKGROUND OF THE INVENTION

1. Field of the Invention

The invention relates to apparatus and methods associated with color measurement and analysis technology and, more particularly, apparatus and methods for compensating color measurement parameters for changes in light source temperature and intensities, and for also compensating such measurements with respect to spectral filter characteristics and the like.

2. Description of Related Art

It is well-known that the term "color" as applied to electromagnetic radiation represents in part the relative energy distribution of radiation within the visible spectrum. That is, light providing a stimulus to the human eye, and having a particular energy distribution, may be perceived as a substantially different color than light of another energy distribution. Concepts relating to the characteristics of color and light waves are the subject of numerous well-known texts, such as *Principles of Color Technology*, Meyer, Jr. and Saltzman (Wiley 1966) and *The Measurement of Appearance*, Hunter and Harold (Wiley 2nd Ed. 1987).

In recent years, the capability of maintaining the "quality of color" has been of significant importance in various industries, such as, for example, the fields of graphic arts, photography and color film processing. For purposes of performing sample testing and other activities in furtherance of maintaining color quality, it is necessary to first determine an appropriate means for "measuring" and "describing" color. A substantial amount of research has been performed during the past 50 years with respect to appropriate methods and standards for color measurement and description.

For purposes of describing color, and from a purely "physical" point of view, the production of color requires three things: a source of light; an object to be illuminated; and, a means for perceiving the color of the object. The means for perceiving the color can be the human eye and brain or, alternatively, electrical and electromechanical apparatus such as photosensitive detectors and associated auxiliary devices utilized for detecting light. In general, it is desirable to provide a means for measuring color so as to assess the manner in which an image will appear to a human observer, or the manner in which an image will perform in a photographic or other type of reproduction printing operation.

Although human perception and interpretation of color can be useful, reliance on such perception and interpretation can be highly subjective. That is, human nature may cause one person's perception of the color of a particular object to be substantially different from the perception of another. In addition, eye fatigue, age and other physiological factors can influence color perception. Further, visual human perception is often insufficient for color description. For example, certain object samples may be visually perceived under one light source as substantially "matching", and yet may actually have very different spectral characteristics and may be perceived as "non-matching" under another light source. In view of the foregoing, it is desirable to employ color measurement and description techniques which are objective in nature, and capable of differentiating among object samples having different color characteristics.

Various devices have been developed and are widely utilized to measure and quantitatively describe color characteristics of object samples. Many of these devices provide measurements related to the spectral characteristics of the samples. Described simplistically, when light is directed onto an object sample to be measured for color, the object may absorb a portion of the light energy, while correspondingly passing through or reflecting (if the object is opaque) other portions of the light. The color characteristics of the object sample will depend in part on the spectral characteristics of the object. That is, the effect of an object on light can be described by its spectral transmittance or reflectance curves (for transparent or opaque materials, respectively). These spectral characteristic curves indicate the fraction of the source light at each wavelength transmitted by or reflected from the materials. Such curves are a means for describing the effect of an object on light in a manner similar to the use of a spectral energy distribution curve for describing the characteristics of a source of light. Instruments utilized for generating such spectral characteristics curves are typically referred to as spectrophotometers.

Although the present invention is disclosed with respect to use in a spectrophotometer, it is worthwhile, for purposes of background, to describe the use of other color measurement devices. In particular, for purposes of background description of typical types of components employed in many color measurement devices, concepts associated with a reflectance densitometer are set forth in the following paragraphs.

In accordance with conventional optical physics, its is known that the proportion of light incident to an object sample and absorbed by such a sample is independent of the light intensity. Accordingly, a quantitative indication of the spectral characteristics of an object sample can be defined as the "transmittance" or "reflectance" of the sample. That is, the transmittance of a substantially transparent object can be defined as the ratio of power transmitted over light power incident to the sample. Correspondingly, for an opaque object sample, the reflectance can be defined as the ratio of power reflected from the object over the incident light power.

For collimated light, these ratios can be expressed in terms of intensities, rather than power. Furthermore, because of the nature of transmittance/reflectance and the optical characteristics of the human eye, it is sometimes advantageous to express these ratios in logarithmic form. Accordingly, one parameter widely used in color technology fields for obtaining a quantitative measurement or "figure of merit" is typically characterized as optical "density." The optical density of an object sample is typically defined as follows:

$$\text{Optical Density} = D = -\log_{10} T \text{ or } -\log_{10} R \qquad \text{(Equation 1)}$$

where T represents transmittance of a transparent object and R represents reflectance of an opaque object. In accordance with the foregoing, if an object sample absorbed 90% of the light incident upon the sample, and the object were opaque, the reflectance would ideally be 10%. The density of such a sample would then be characterized as unity. Correspondingly, if 99.9% of the light were absorbed, the reflectance would be 0.1% and the density would be 3.

Similarly, the density of an "ideal" object reflecting 100% of the light incident upon the object would be 0.

To provide a relative measurement of color, it is possible to utilize the principles of optical density, without requiring measurement or knowledge of the absolute values of total incident light intensity or reflectance. That is, for example, it is possible to obtain relative color measurements among a series of object samples by utilizing a particular geometric configuration of light, object sample and reflectance or transmittance detector for each measurement, and standardizing the measurements in some desired manner.

In brief summary, optical density is a measurement of the modulation of light or other radiant flux by an object sample, such as a given area of a photographic print. Density measurements provide a means to assess the manner in which an image will appear to a human observer, or the way an image will perform in a film processing operation. Density measurements can be utilized to produce sensitometric curves to evaluate various printing and reproduction characteristics, as well as utilization to control various photographic operations, such as film processing.

For purposes of measuring optical densities, it is well-known to employ a device typically characterized as a "densitometer." These densitometers are often categorized as either "reflection" densitometers, employed for optical density measurements of opaque objects, or are otherwise characterized as "transmittance" densitometers. Transmittance densitometers are employed for determining spectral characteristics of various non-opaque materials.

FIG. 1 illustrates a simplified schematic representation of a known reflection densitometer configuration 100. A configuration of this type is described in detail in the commonly assigned and currently pending U.S. patent application Ser. No. 534,205 filed Jun. 7, 1990, which is a continuation of commonly assigned U.S. patent application Ser. No. 105, 424 filed Oct. 5, 1987 and now abandoned. Densitometer apparatus of the type shown in FIG. 1 are characterized as reflection densitometers, and utilized to provide color density measurements of opaque materials as previously described.

Referring specifically to FIG. 1, and to numerical references therein, the densitometer apparatus 100 includes a light source unit 102 having a source light 104. With respect to optical density measurements in photography, color film processing, and other industrial fields, various standards have been developed for densitometer light source illuminants. For example, densitometer light source standards have previously been described in terms of a tungsten lamp providing an influx from a lamp operating at a Planckian distribution of 3000° K. Other suggested standards have been developed by the American National Standards Institute ("ANSI") and the International Organization for Standardization ("ISO"). These source light densitometer standards are typically defined in terms of the spectral energy distribution of the illuminant. The source light 104 preferably conforms to an appropriate standard and can, for example, comprise a filament bulb meeting a standard conventionally known in the industry as 2856K ANSI. Power for the source light 104 and other elements of the densitometer apparatus 100 can be provided by means of conventional rechargeable batteries or, alternatively, interconnection to AC utility power.

The source light 104 projects light through a collimating lens 106 which serves to focus the electromagnetic radiation from the source light 104 into a narrow collimated beam of light rays. Various types of conventional and well-known collimating lenses can be employed. The light rays transmitted through the collimating lens 106 project through an aperture 108. The dimensions of the aperture 108 will determine the size of the irradiated area of the object sample under test.

Various standards have been defined for preferable sizes of the irradiated area. Ideally, the aperture 108 is of a size such that the irradiance is uniform over the entire irradiated area. However, in any physically realizable densitometer arrangement, such uniform irradiance cannot be achieved. Current standards suggest that the size of the irradiated area should be such that irradiance measured at any point within the area is at least 90% of the maximum value. In addition, however, aperture size is typically limited to the size of the color bar or color patch area to be measured, and is also sized so as to reduce stray light.

The light rays emerging from the aperture 108 (illustrated as rays 110 in FIG. 1) are projected onto the irradiated area surface of an object sample 112 under test. The sample 112 may be any of numerous types of colored opaque materials. For example, in the printing industry, the sample 112 may be an ink-on-paper sample comprising a portion of a color bar at the edge of a color printing sheet. Further, with respect to the illustrative embodiment of a densitometer apparatus employing the principles of the invention as described in subsequent paragraphs herein, the sample 112 may be a control strip employed in the color film processing industry.

As the light rays 110 are projected onto the object sample 112, electromagnetic radiation shown as light rays 114 will be reflected from the sample 112. Standard detection configurations have been developed, whereby reflected light is detected at a specific angle relative to the illumination light rays 110 projected normal to the plane of the object sample 112. More specifically, standards have been developed for detection of reflected light rays at an angle of 45° to the normal direction of the light rays 110. This angle of 45° has become a standard for reflectance measurements, and is considered desirable in that this configuration will tend to maximize the density range of the measurements. In addition, however, the 45° differential also represents somewhat of a relatively normal viewing configuration of a human observer (i.e. illumination at a 45° angle from the viewer's line of sight).

For purposes of providing light detection, a spectral filter apparatus 116 is provided. The filter apparatus 116 can include a series of filters 118, 120 and 122. The filters 118, 120 and 122 are employed for purposes of discriminating the cyan, magenta and yellow spectral responses, respectively. That is, each of the filters will tend to absorb light energy at frequencies outside of the bandwidth representative of the particular color hue of the filter. For example, the cyan filter 118 will tend to absorb all light rays, except for those within the spectral bandwidth corresponding to a red hue. By detecting reflected light rays only within a particular color hue bandwidth, and obtaining an optical density measurement with respect to the same, a "figure of merit" can be obtained with respect to the quality of the object sample coloring associated with that particular color hue.

It is apparent from the foregoing that the actual quantitative measurement of color density or color reflectance is dependent in substantial part on the spectral transmittance characteristics of the filters. Accordingly, various well-known standards have been developed with respect to spectral characteristics of densitometer filters. For example, one standard for densitometer filters is known as the ANSI status T color response. The spectral response characteristics of filters meeting this standard are relatively wide band (in the range of 50–60 namometers (nms) bandwidth) for each of the cyan, magenta and yellow color hues. Other spectral response characteristic standards include, for example, what is known as G-response, which is somewhat similar to status T, but is somewhat more sensitive to respect to yellow hues. An E-response represents a European response standard.

Although the filters 118, 120 and 122 are illustrated in the embodiment shown in FIG. 1 as the cyan, magenta and yellow color shades, other color shades can clearly be employed. These particular shades are considered somewhat preferable in view of their relative permanence, and because they comprise the preferred shades for use in reflection densitometer calibration. However, it is apparent that different shades of red, blue and yellow, as well as entirely different colors, can be utilized with the densitometer apparatus 100.

The spectral filters 118, 120 and 122 may not only comprise various shades of color, but can also be one of a number of several specific types of spectral response filters. For example, the filters can comprise a series of conventional Wratten gelatin filters and infrared glass. However, various other types of filter arrangements can also be employed.

The spectral filters 118, 120 and 122 are preferably positioned at a 45° angle relative to the normal direction from the plane of the object sample 112 under test. In the particular example shown in FIG. 1, each of these filters is maintained stationary and utilized to simultaneously receive light rays reflected from the object sample 112. Further, although the particular example illustrated in FIG. 1 may include a stationary object sample 112, the example embodiment of a densitometer apparatus employing principles of the invention as described in subsequent paragraphs herein can include an object sample which is continuously moving relative to the spectral filter arrangement. In such an instance, the actual spectral filter measurements may be obtained simultaneously or, alternatively, in sequence.

As further shown in FIG. 1, the portion of the reflected light rays 114 passing through the filters 118, 120 and 122 (shown as light rays 124, 126 and 128, respectively) impinge on receptor surfaces of photovoltaic sensor cells. The sensor cells are illustrated in FIG. 1 as sensors 132, 134 and 136 associated with the spectral filters 124, 126 and 128, respectively. The sensors 132, 134 and 136 can comprise conventional photoelectric elements adapted to detect light rays emanating through the corresponding spectral filters. The sensors are further adapted to generate electrical currents having magnitudes proportional to the intensities of the sensed light rays. As illustrated in FIG. 1, electrical current generated by the cyan sensor 132 in response to the detection of light rays projecting through the filter 118 is generated on line pair 138. Correspondingly, electrical current generated by the magenta sensor 134 is applied to the line pair 140, while the electrical current generated by the yellow sensor 136 is applied as output current on line pair 142. Photoelectric elements suitable for use as sensors 136, 138 and 140 are well-known in the art, and various types of commercially-available sensors can be employed.

The magnitude of the electrical current on each of the respective line pairs will be proportional to the intensity of the reflected light rays which are transmitted through the corresponding spectral filter. These light rays will have a spectral distribution corresponding in part to the product of the spectral reflectance curve of the object sample 112, and the spectral response curve of the corresponding filter. Accordingly, for a particular color shade represented by the spectral response curve of the filter, the magnitude of the electrical current represents a quantitative measurement of the proportional reflectance of the object sample 112 within the frequency spectrum of the color shade.

As further shown in FIG. 1, the sensor current output on each of the line pairs 138, 140 and 142 can be applied as an input signal to one of three conventional amplifiers 144, 146 and 148. The amplifier 144 is responsive to the current output of cyan sensor 132 on line pair 138, while amplifier 146 is responsive to the sensor current output from magenta sensor 134 on line pair 144. Correspondingly, the amplifier 148 is responsive to the sensor current output from yellow sensor 136 on line pair 142. Each of the amplifiers 144, 146 and 148 provides a means for converting low level output current from the respective sensors on the corresponding line pairs to voltage level signals on conductors 150, 152 and 154, respectively. The voltage levels of the signals on their respective conductors are of a magnitude suitable for subsequent analog-to-digital (A/D) conversion functions. Such amplifiers are well-known in the circuit design art, and are commercially available with an appropriate volts per ampere conversion ratio, bandwidth and output voltage range. The magnitudes of the output voltages on lines 150, 152 and 154 again represent the intensities of reflected light rays transmitted through the corresponding spectral filters.

Each of the voltage signal outputs from the amplifiers can be applied as an input signal to a conventional multiplexer 156. The multiplexer 156 operates so as to time multiplex the output signals from each of the amplifiers 144, 146 and 148 onto the conductive path 158. Timing for operation of the multiplexer 156 can be provided by means of clock signals from master clock 160 on conductive path 162. During an actual density measurement of an object sample, the densitometer 100 will utilize a segment of the resultant multiplexed signal which sequentially represents a voltage output signal from each of the amplifiers 144, 146 and 148.

The resultant multiplexed signal generated on the conductive path 158 is applied as an input signal to a conventional A/D converter 164. The A/D converter 164 comprises a means for converting the analog multiplexed signal on conductor 158 to a digital signal for purposes of subsequent processing by central processing unit (CPU) 166. The A/D converter 164 is preferably controlled by means of clock pulses applied on conductor 168 from the master clock 160. The clock pulses operate as "start" pulses for performance of the A/D conversion. The A/D converter 164 can be any suitable analog-to-digital circuit well-known in the art and can, for example, comprise 16 binary information bits, thereby providing a resolution of 65K levels per input signal.

The digital output signal from the A/D converter 164 can be applied as a parallel set of binary information bits on conductive paths 170 to the CPU 166. The CPU 166 can provide several functions associated with operation of the densitometer apparatus 100. In the embodiment described herein, the CPU 166 can be utilized to perform these functions by means of digital processing and computer programs. In addition, the CPU 166 can be under control of clock pulses generated from the master clock 160 on path 172. However, a number of the functional operations of CPU 166 could also be provided by means of discrete hardware components.

In part, the CPU 166 can be utilized to process information contained in the digital signals from the conductive paths 170. Certain of this processed information can be generated as output signals on conductive path 176 and applied as input signals to a conventional display circuit 178. The display circuit 178 provides a means for visual display of information to the user, and can be in form of any one of several well-known and commercially-available display units.

In addition to the CPU 166 receiving digital information signals from the conductive paths 170, information signals can also be manually input and applied to the CPU 166 by means of a manually-accessible keyboard circuit 180. The user can supply "adjustments" to color responses by means of entering information through the keyboard 180. Signals representative of the manual input from the keyboard 180 are applied as digital information signals to the CPU 166 by means of conductive path 182.

In general, the most commonly used instruments for "measuring" color now in commercial use are spectrophotometers, colorimeters and densitometers. While the three types of instrumentation are employed to measure reflected or transmitted light, a spectrophotometer typically measures light at a number of points on the visible spectrum, thereby resulting in a curve. With reference to FIG. 1, a spectrophotometer may have a similar configuration to the densitometer 100, but instead of having only three pairs of filters and photodiodes, a spectrophotometer may have, for example, sixteen or more pairs of filter and photodiode configurations. Each of the filters would be associated with a substantially separate portion of the visible light spectrum, for purposes of obtaining a curve representative of reflectance (for opaque objects) characteristics of various object samples. Typically, with a spectrophotometer, the output variable represented by the curve (as a function of wavelength) represents a percentage reflectance value. A spectrophotometer is considered essential in the color formulation of many products. Such products can vary from solid, opaque objects (such as ceramics and metals) to transparent liquids, such as varnishes and dye solutions.

A colorimeter, in contrast to a spectrophotometer, typically is utilized to measure light in a manner similar to the human eye, i.e. with utilization of red, green and blue (or similar colors) receptors. Colorimeters are utilized for many applications, including the measurement of printed colors on products such as packages, labels and other materials, where a product's appearance may be considered substantially critical for buyer acceptability. Such colorimeters will typically provide output in the form of tristimulus values or, alternatively, in the form of other values which tend to relate more specifically to appearance attributes of colors. For example, chromaticity coordinates are often utilized.

Densitometers (such as the densitometer 100 previously described herein) are similar to colorimeters, except that the response characteristics for densitometers are typically designed for purposes of measuring specific materials, such as printing inks and photographic dyes. For example, a reflection densitometer may be utilized to measure the color bar on a press sheet, for purposes of monitoring color reproduction. As previously described, output variables associated with a reflection densitometer may be in the form of cyan, magenta and yellow color variables for density and other characteristics.

As is well-known in the art, color measuring apparatus are preferably first "calibrated" to provide desired spectral response characteristics for a given set of spectral filters and light sources. In known densitometer systems, for example, the "zero density" condition and the response "slope" for a particular densitometer and filter set can be provided as parameters comprising manual input data for the densitometer. For example, to provide what can be characterized as an "initial condition" of zero density for each individual spectral filter, an object sample comprising a "white" reference patch (representing substantial reflection) can be measured for each of the individual filters. The densitometer gain adjustments can then be manually adjusted so as to provide a standardized densitometer reading for the patch. Correspondingly, with the logarithmic density measurement assumed to be linear, the "slope" of the densitometer response can be set by means of viewing a "black" patch (representing a substantial absorption) and setting the densitometer reading to a standardized "maximum" for the patch measurement for each of the filters.

Although the foregoing represents a means for calibrating zero density level measurements and density slope sensitivity in a densitometer arrangement, known color measuring devices employing these and other calibration procedures still suffer from several substantial disadvantages. For example, when standards are provided for adjusting the density level readings for particular filter types in a densitometer, such standards assume an "ideal" filter. However, any physically realizable spectral filter arrangement will vary from the ideal. Such filter manufacturing errors can correspondingly result in errors in the measurement of densities and other spectral characteristics.

Problems associated with various known calibration procedures result from several other considerations, in addition to the problems associated with manufacturing tolerances of spectral filter arrangements. For example, specification standards for various types of spectral filter arrangements call for certain types of light and color temperature, in addition to other illuminant parameters. However, manufacturing errors exist with respect to all physically realized illuminants. Furthermore, as a color measuring device is used over a period of time, filament lamps will tend to drift.

In addition, as light source lamps increase in temperature during use, the light intensity will tend to decrease. Accordingly, reflectance intensity will also tend to decrease. For these reasons, it is known to employ what are commonly referred to as "side sensors" during the color measurement process. The side sensors are employed to measure the source light or lamp intensity, and provide signals for purposes of determining calibration or lamp compensation parameters. These parameters are employed to generate compensation or calibration constants which are applied, by data processing or similar means, to actual color measurements for purposes of providing compensated measurements.

Various types of compensation and calibration arrangements are known for utilization in color measuring devices. For example, in Suigyama et al, U.S. Pat. No. 4,773,761 issued Sep. 27, 1988, a photoelectric colorimeter is disclosed having a series of photodiodes for measurement of an object sample, and a corresponding series of photodiodes for measurement of the light source. A measured value of the object value is divided by a measured value of the light source, for purposes of attempting to cancel fluctuations of the light source.

Light from the object sample and from the light source is analyzed with respect to primary color elements with a series of optical filters. The color elements are analyzed and detected by photodiodes, and then converted into electrical signals by corresponding photoelectric converter circuits. Signals representative of the color elements are stored in conventional sample/hold circuitry, and applied through a series of gates to a comparator. A central processing unit determines tristimulus data from the electrical signals.

Upon initiation of use of the colorimeter, a calibration operation is performed. In the Suigyama et al arrangement, the colorimeter includes ten calibrating channels, so that the calibration arrangement can be performed with respect to ten kinds of reference calibration samples. The operator first inputs tristimulus values for the reference calibration sample by means of numerical keys on a keyboard. The reference calibration sample is then measured to obtain measured tristimulus values, and calibration constants are calculated as a ratio of the manually input tristimulus values to the measured tristimulus values.

In the Suigyama et al arrangement, the manually input tristimulus values of the reference calibrating sample are converted into a different color space and stored in memory. Following the calibration for channel zero, the operator prepares a calibration reference sample for calibrating each of the other channels, with the input of tristimulus values by means of the numerical keys. Again, the reference calibration samples are measured to obtain actual measured tristimulus values, and these values are then corrected utilizing the calibration constants of channel zero. Calibration constants for each of the individual channels are then calculated by substituting the values obtained from utilization of the calibration constants for channel zero. That is, each of the calibration constants for the channels is comprised of a ratio of the manually input tristimulus values for the channel to the tristimulus values obtained through use of the calibration constants for channel zero. Again, the tristimulus values for the reference calibrating sample for each of the other channels are then converted to a different color space.

SUMMARY OF THE INVENTION

In accordance with one aspect of the invention, a compensation method is adapted for use in color measuring apparatus for measuring color characteristics of actual object samples under test. The method includes the employment of a reference sample, and the projection of light toward the reference sample through the use of a light source means. A plurality of measurements of the reference sample are performed, with the measurements providing measured color characteristic values of the sample for a series of spectral segments across a light spectrum. A plurality of side sensor measurements are also performed, employing at least one side sensor. The side sensor measurements provide measured light source intensity values indicative of the intensity of the light source means.

Filter compensation coefficients are determined for the segments as functions of certain of the measured color characteristic values of the reference sample, and as functions of certain of the measured light source intensity values. Measurements of color characteristic values of actual object samples under test are compensated as functions at least in part of the filter compensation coefficients.

The plurality of measurements of the reference sample can provide timed-sequenced sets of the measured color characteristic values of the reference sample. Each set of the measured color characteristic values can comprise a measured color characteristic value for each spectral segment of the series of spectral segments. The plurality of side sensor measurements can comprise a separate side sensor measurement for each set of the sets of measured color characteristic values. Further, the one side sensor can be associated with an associated filter maintained in a stationary position relative to the side sensor during performance of the plurality of side sensor measurements.

In determining the filter compensation coefficients, a separate filter compensation coefficient can be determined for each of the segments as a function of certain of the measured color characteristic values of the reference sample associated only with that particular segment, and as a function of certain of the measured light source intensity values. The measurements of the color characteristic values of the actual object samples under test can be compensated without requiring any matching of spectral response characteristics of the side sensor with any spectral response characteristics of means employed for performing the plurality of measurements of the reference sample.

Each of the plurality of side sensor measurements can be performed employing only a single side sensor and an associated filter. The spectral response characteristic of the single side sensor and the associated filter can be identical for each of the plurality of side sensor measurements. The associated filter can be maintained in a stationary position relative to the side sensor during performance of the side sensor measurements.

In accordance with another aspect of the invention, initiation of performance of the plurality of measurements of the reference sample can be prohibited, and the initiation of performance of the plurality of side sensor measurements can be prohibited, until a predetermined period of time has elapsed since any prior measurements of the reference sample or prior side sensor measurements.

Each of the filter compensation coefficients can be determined in accordance with the following:

$$CCx = ((RS1x/RSNx) - 1)/((SS1/SSN) - 1)$$

where CCx is the filter compensation coefficient for segment x, RS1x is a first measured color characteristic value of said reference sample for segment x, RSNx is a last measured color characteristic value of said reference sample for segment x, SS1 is a measured light source intensity value for a first one of said plurality of side sensor measurements, and SSN is a measured light source intensity value for a last one of said plurality of said side sensor measurements.

The plurality of side sensor measurements can correspond in number to the plurality of measurements of the reference sample. The plurality of measurements of the reference sample can provide timed-sequenced sets of the measured color characteristic values of the reference sample. Each of the plurality of side sensor measurements can correspond in time to one of the timed-sequenced sets of the measured color characteristic values.

The timed-sequenced sets and the plurality of side sensor measurements can be five in number. Further, the plurality of measurements of the reference sample and the plurality of side sensor measurements can be performed in a timed-sequence. In addition, the period of time between measurements of each of the timed-sequences can be approximately 3 seconds. In addition, the series of spectral segments can comprise sixteen in number.

In accordance with another aspect of the invention, for each of the spectral segments, and for each of the plurality of measurements of the reference sample, a normalized color characteristic value can be determined as a function of the measured color characteristic value for that particular segment and measurement of the reference sample, and as a function of the filter compensation coefficient for that particular segment and certain of the measured light source intensity values. The measurements of the color characteristic values of the actual object samples under test for a particular segment can be compensated, as a function in part of the normalized color characteristic values.

Each of the normalized color characteristic values can be determined in accordance with the following:

$$RScxa = RSxa[(((SS1/SSa) - 1)CCx) + 1]$$

where RScxa is a normalized color characteristic value for segment x and measurement a, RSxa is a measured color characteristic value of said reference sample for segment x and measurement a, SS1 is a measured light source intensity value for a first one of said plurality of side sensor measurements, SSa is a measured light source intensity value for a current one of said plurality of side sensor measurements, and CCx is a filter compensation coefficient for a current spectral segment.

The compensation method can also include the determination of a scale factor for each of the segments. Each of the scale factors can represent the conversion of a measured color characteristic quantity to a color characteristic value relative to a desired color characteristic value. Measurements of the color characteristic values of actual object samples under test can be compensated for a particular segment, as a function in part of the scale factor for the particular segment.

In accordance with another aspect of the invention, the method can include the input or prestorage of reference data indicative of expected or desired spectral characteristics of the reference sample, for each of the series of spectral segments.

The scale factor for each of the segments can be determined in accordance with the following:

$$WSx=[(RSc1x+RSc2x+\ldots RScNx)/N]/WRx$$

where WSx is a scale factor for segment x, RSc1x is a normalized color characteristic value for a first one of said plurality of measurements of said reference sample for segment x, RSc2x is a normalized color characteristic value for a second one of said plurality of measurements of said reference sample for segment x, and RScNx is a normalized color characteristic value for a last one of said plurality of measurements of said reference sample and segment x, and WRx is a desired color characteristic value for segment x.

The measurements of the color characteristic values of the actual object samples under test for a particular segment can be compensated as a function in part of the scale factor for the particular segment.

The color measuring apparatus can be a spectrophotometer. The measured color characteristic values of the reference sample for each of a series of spectral segments across a light spectrum can be indicative of measured reflectance values of light reflected from the reference sample.

In accordance with the invention, the measurements of the color characteristic values of the actual object samples under test can be compensated in accordance with the foregoing:

$$Rx=WSx[RSx((CCx((SS1/SS)-1))+1)]$$

where Rx is a compensated measurement of color characteristic values of said object samples under test, WSx represents a scale factor for segment x, RSx represents an actual measured color characteristic value of said object sample under test for segment x, CCx represents one of said filter compensation coefficients for segment x, SS1 is a measured light source intensity value for a first one of said plurality of side sensor measurements, and SS is a current measured light source intensity value.

The compensation method can also include determination of temperature values of the light source means or area adjacent the light source means. Measurements of the color characteristic values of the actual object samples under test can be compensated as a function at least in part of the temperature values. The method can also include determination of a temperature coefficient for each segment of the series of spectral segments. Measurements of color characteristic values for a particular segment of the actual object samples under test can be compensated as a function of the temperature coefficient for the particular segment, a then current one of the temperature values and at least one temperature value obtained during performance of the plurality of measurements of the reference sample.

The compensation method can also include determination of a temperature coefficient associated specifically with the side sensor. The measurements of color characteristic values of actual object samples under test can be compensated as a function of the temperature coefficient, a then current one of the temperature values and at least one temperature value obtained during performance of the plurality of side sensor measurements.

In accordance with another aspect of the invention, a color measuring apparatus for use in measuring color characteristics of actual object samples under test, and for compensating measurements of the color characteristics through the use of a reference sample is defined. The apparatus includes at least one light source for projecting light toward the reference sample. Color characteristic measuring means are provided for performing a plurality of measurements of the reference sample. The color characteristic measuring means also generate signals representative of measured color characteristic values of the reference sample for a series of spectral segments across a light spectrum. At least one side sensor is provided for performing a plurality of side sensor measurements and generating signals representative of measured light source intensity values indicative of the intensity of the light source.

A processor is provided which is responsive to the signals representative of the measured color characteristic values and also responsive to the signals representative of the measured light source intensity values for determining filter compensation coefficients for the segments. The coefficients are determined as functions of certain of the measured color characteristic values of the reference sample and as functions of certain of the measured light source intensity values. The processor includes means for compensating measurements of color characteristic values of the actual object samples under test as functions at least in part of the filter compensation coefficients.

The side sensor of the apparatus can be associated with an associated filter maintained in a stationary position relative to the side sensor during performance of the plurality of side sensor measurements. The plurality of side sensor measurements can be performed employing only a single side sensor and an associated filter. In this manner, the spectral response characteristic of the single side sensor and the filter is identical for each of the plurality of side sensor measurements. Further, the associated filter can be maintained in a stationary position relative to the single side sensor during performance of the plurality of side sensor measurements.

The apparatus can also include means for prohibiting initiation of performance of the plurality of measurements of the reference sample. In addition, the means can prohibit initiation of performance of the plurality of side sensor measurements, until a predetermined period of time has elapsed since any prior measurements of the reference sample or prior side sensor measurements.

The processor can include means, for each of the spectral segments and for each of the plurality of measurements of the reference sample, for determining a normalized color characteristic value as a function of the measured color characteristic value for that particular segment and measurement of the reference sample, and as a function of the filter compensation coefficient for that particular segment and certain of the measured light source intensity values. The means for compensating the measurements of the color characteristic values of the actual object samples under test can include means for compensating the measurements of the color characteristic values of object samples under test for a particular segment as a function in part of the normalized color characteristic values.

The processor can also include means for determining a scale factor for each of the segments, with each of the scale factors representing the conversion of a measured color characteristic quantity to a color characteristic value relative to a desired color characteristic value. Means can also be provided for compensating the measurements of the color characteristic values of the actual object samples under test for a particular segment, as a function in part of the scale factor for the particular segment.

The apparatus can include means for inputting reference data indicative of expected or desired spectral characteristics of the reference sample, for each segment of the series of spectral segments. In addition, the apparatus can include means for storing reference data indicative of expected or desired spectral characteristics of the reference sample, for each segment of the series of spectral segments.

The apparatus can also include means for determining temperature values of the light source or area adjacent the light source. Means can be provided for compensating the measurements of the color characteristic values of the actual object samples under test as a function at least in part of the temperature values.

In addition, the apparatus can include means for determining a temperature coefficient for each segment of the series of spectral segments. Means can also be provided for compensating measurements of color characteristic values for a particular segment of the actual object samples under test as a function of the temperature coefficient for the particular segment, a then current one of the temperature values and at least one temperature value obtained during performance of the plurality of measurements of the reference sample.

Further, the apparatus can include means for determining a temperature coefficient associated with the side sensor. Means can also be provided for compensating measurements of the color characteristic values of the actual object samples under test as a function of the temperature coefficient, a then current one of the temperature values and at least one temperature value obtained during performance of the plurality of side sensor measurements.

BRIEF DESCRIPTION OF THE DRAWINGS

The invention will now be described with respect to the drawings, in which.

DESCRIPTION OF THE PREFERRED EMBODIMENT

Figure 2:
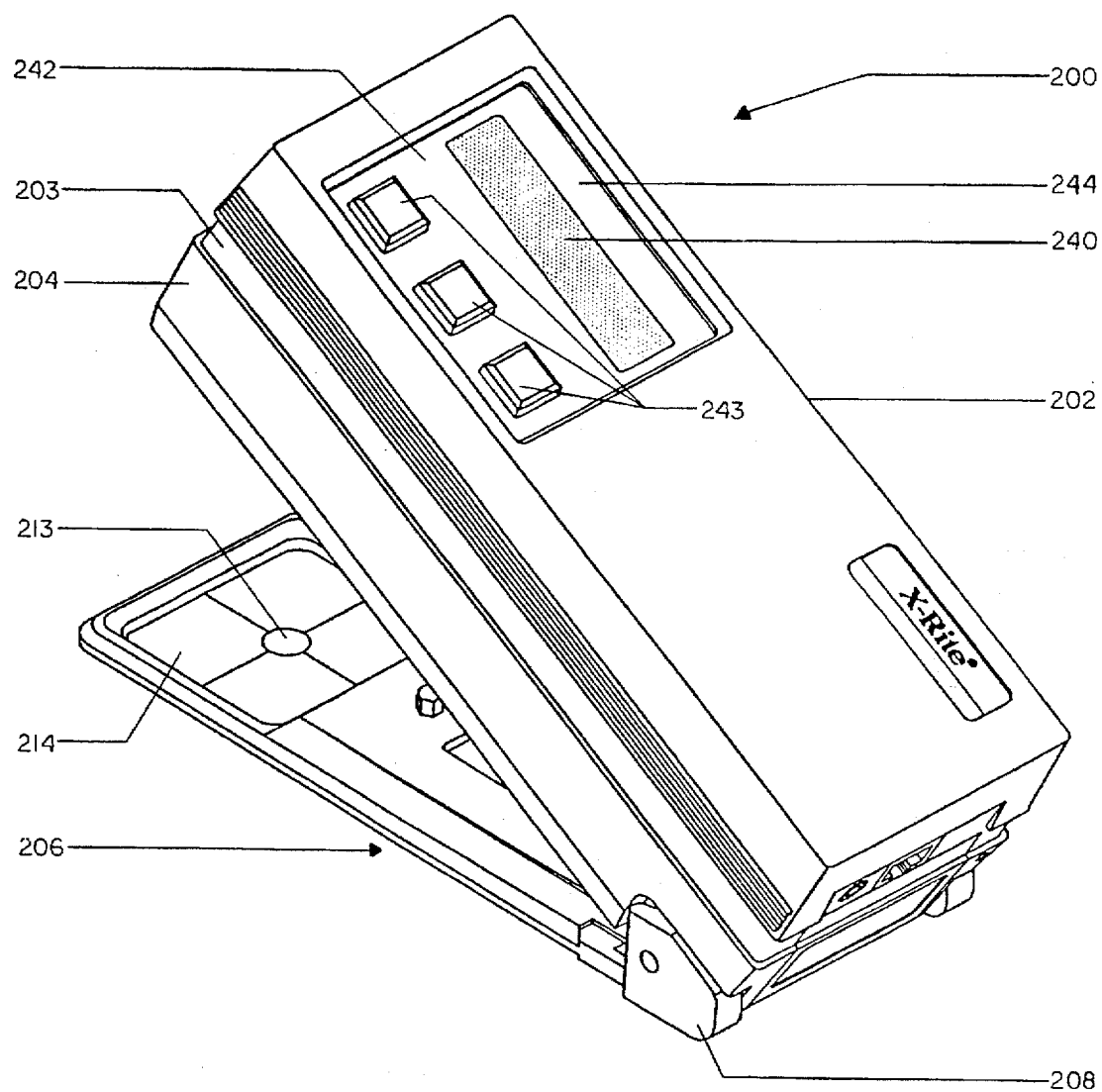
FIG. 2 is a perspective view of a spectrophotometer apparatus which can be utilized with a calibration arrangement in accordance with the invention.
Figure 3:
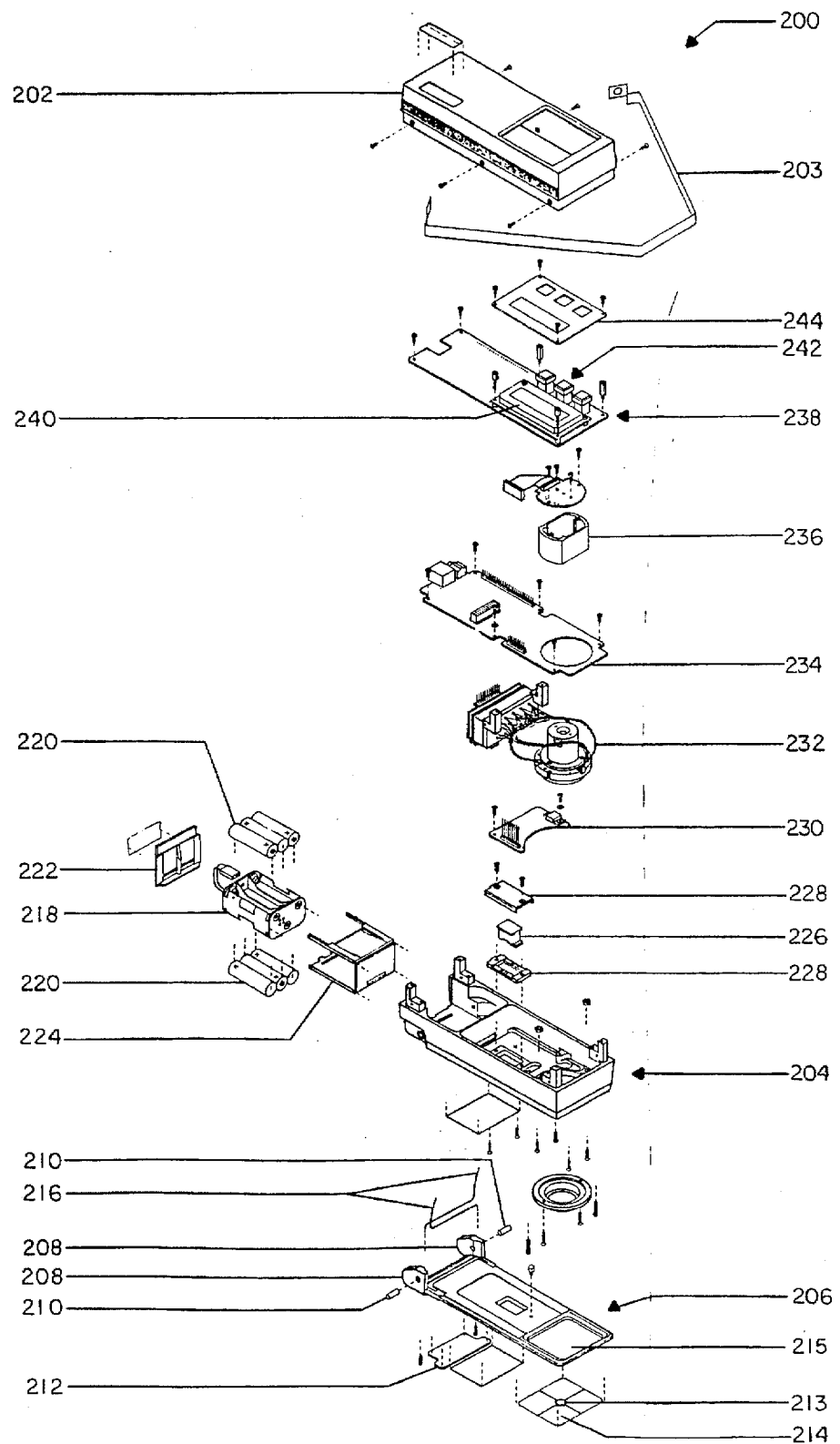
FIG. 3 is an exploded view of the internal components of the spectrophotometer apparatus shown in FIG. 2.

The principles of the invention relate to apparatus and methods for spectrophotometer calibration and are disclosed, by way of example, in a spectrophotometer apparatus 200 as illustrated in FIGS. 2 and 3. Spectrophotometer apparatus of the type shown in FIGS. 2 and 3 are characterized as reflection spectrophotometers and utilized to provide spectral response characteristics of object samples as previously described in the section entitled "Background of the Invention." As described in greater detail herein, the spectral response characteristics are obtained by projecting light toward the object sample and then measuring the proportion of light reflected from the object sample within each of a series of spectral segments across the visible light spectrum. In accordance with the invention, the spectrophotometer apparatus 200 provides a means for calibrating or correcting reflectance measurement readings by performing a series of timed-sequence measurements of a reference sample, and determining color measurements of actual object samples as a function of the sequence measurements, compensation parameters obtained from the timed-sequence measurements, and corresponding measurements of light source intensities.

An exemplary physical structure of the spectrophotometer apparatus 200 is illustrated in relative simplicity in FIGS. 2 and 3. Referring specifically to FIG. 2, the spectrophotometer apparatus 200 comprises a relatively compact structure suitable for use on a desk top or similar work surface. The spectrophotometer apparatus 200 includes an upper cover 202 which may have a trim strip 203 positioned therearound. Located below the upper cover 202 is a housing subassembly 204 adapted to house various components of the spectrophotometer apparatus 200.

The apparatus 200 also includes a lower shoe 206 adapted to be positioned flat on the desk top or work surface. The shoe 206 is pivotally interconnected to the housing subassembly 204 by means of hinge brackets 208 and interconnecting dowels 210. A shoe pad 212 is positioned below the lower shoe 206. A shoe window 214 is positioned in an aperture 215 of the lower shoe 206. Object samples under test and reference samples for which color measurements are to be obtained are positioned so as to be centrally located relative to the reference position 213 of the shoe window 214. The cover 202 and housing subassembly 204 are maintained in a biased position pivotally angled relative to the lower shoe 206 by means of lift springs 216.

The spectrophotometer apparatus 200 can also include a relatively conventional battery holder 218 adapted to mount a series of batteries 220 for purposes of providing DC battery power to the apparatus 200. The batteries 220 are enclosed by means of an access cover 222, and the battery configuration is mounted within the housing subassembly 204 within a battery insulator 224.

Referring primarily to FIG. 3, the spectrophotometer apparatus 200 also includes a lock button 226 positioned within a pair of upper and lower lock button guides 228. The lock button 226 can be utilized to secure the cover 202, housing subassembly 204 and associated components in a measuring position relative to the lower shoe 206.

As further shown in FIG. 3, the spectrophotometer apparatus 200 also includes a lamp/side sensor board assembly 230 which is utilized to mount an optics assembly 232 for the spectrophotometer apparatus 200. The optics assembly 232 includes various electrical components of the apparatus 200 which will be described in greater detail with reference to FIG. 4 in subsequent paragraphs herein.

Also shown in FIG. 3 is a main PC board assembly 234 through which is mounted a side sensor shield 236. An upper display board assembly 238 is also provided. The upper display board assembly 238 mounts a visual display device 240 which can comprise a conventional LCD display device. In addition, the display board assembly 238 also mounts a keyboard 242 having a series of key switches 243. The key switches 243 associated with the keyboard 242 can be conventional switches for providing manual input entry for the spectrophotometer apparatus 200. A display cover 244 is utilized to aesthetically cover the visual display device 240 and keyboard 242 in a manner shown primarily in FIG. 2.

Figure 1:
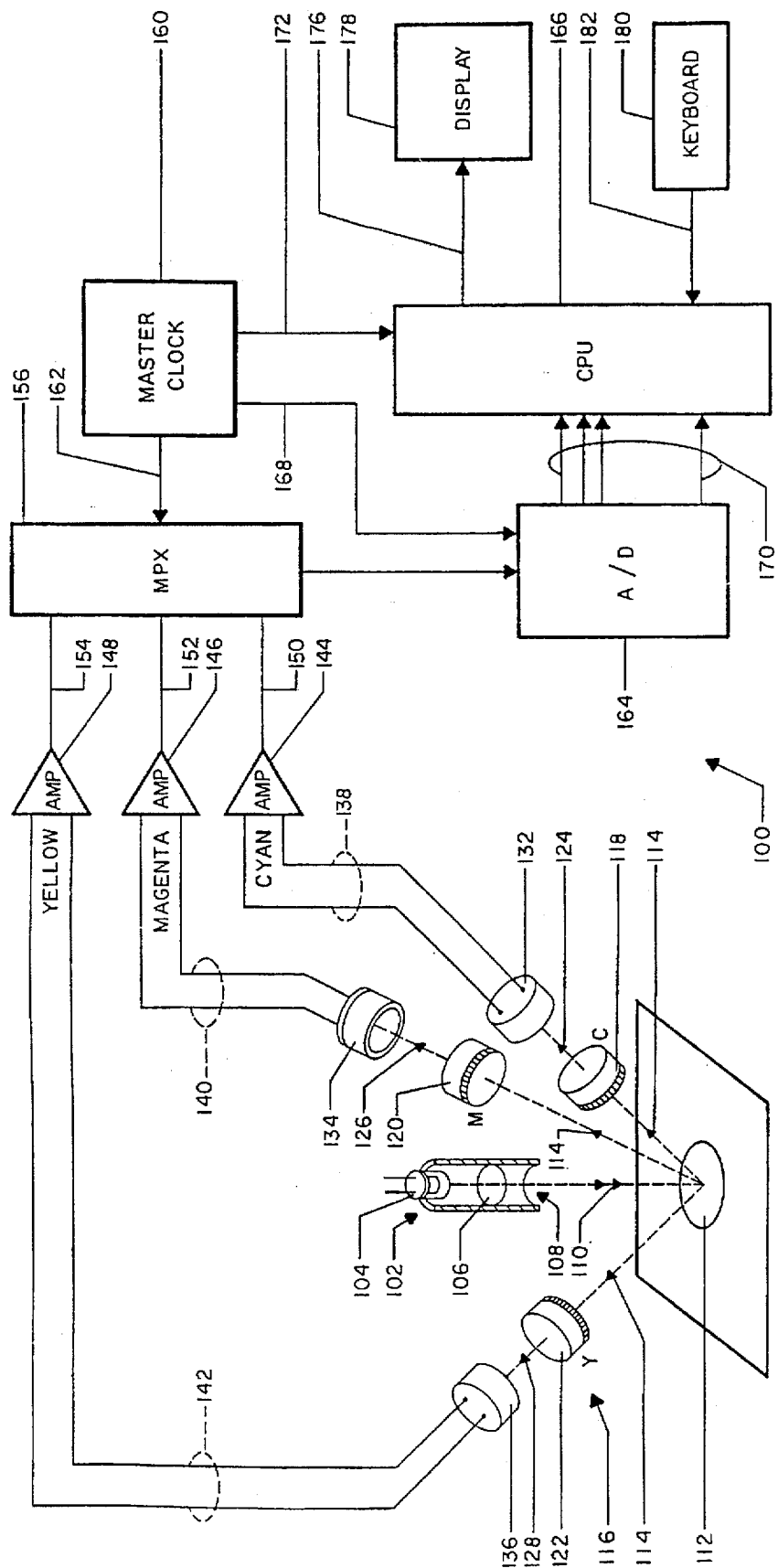
FIG. 1 is an illustrative embodiment of a prior art color measuring device comprising a densitometer.
Figure 4:
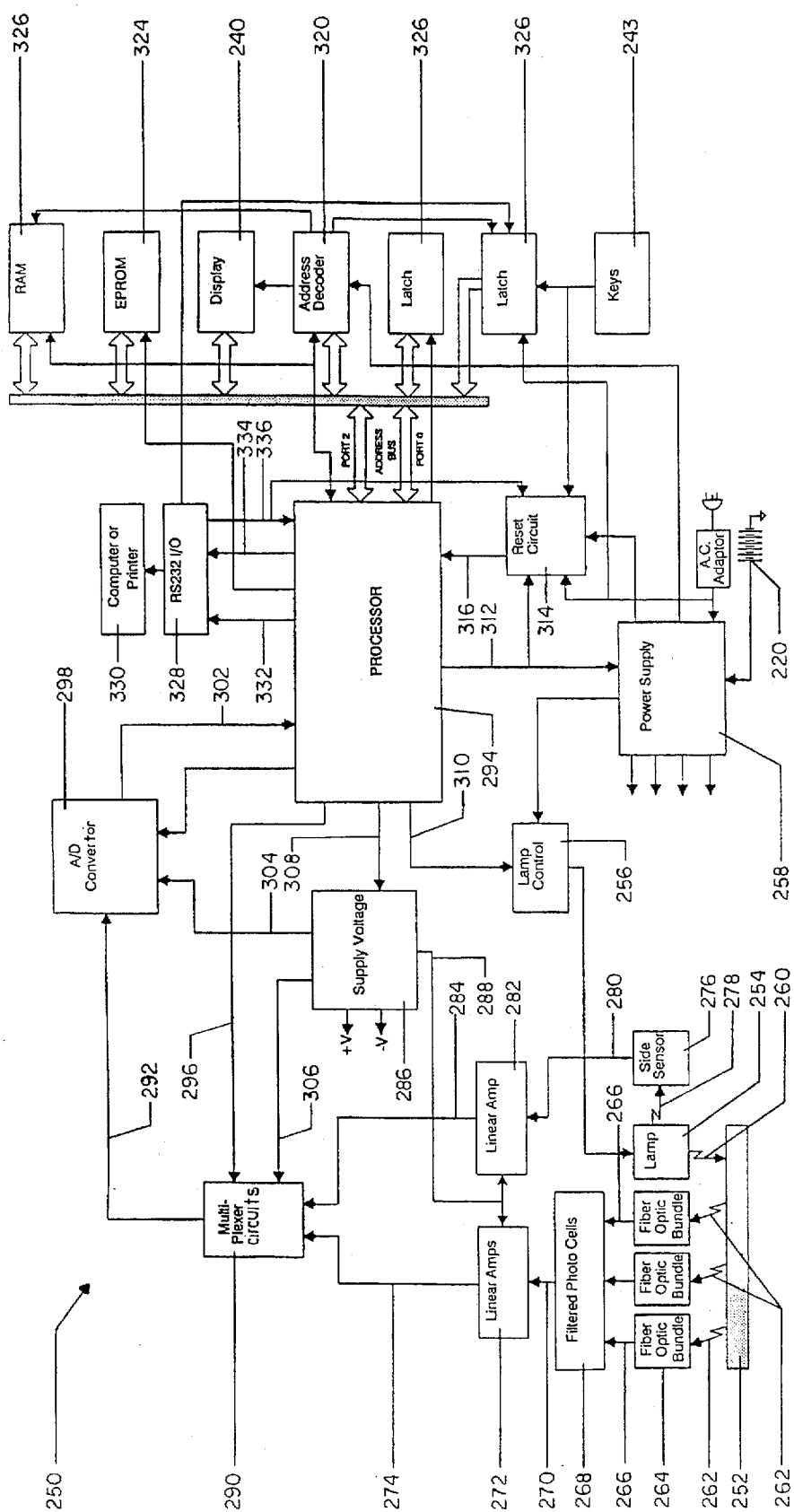
FIG. 4 is a partially schematic diagram of circuit elements of the spectrophotometer system shown in FIG. 2.

A circuit configuration 250, comprising an exemplary embodiment of the circuitry of spectrophotometer apparatus 200 which can be utilized in accordance with the invention, is primarily illustrated in FIG. 4. A number of the components of the circuit configuration 250 are similar in structure and function to components of the densitometer apparatus 100 previously described with respect to FIG. 1 in the section entitled "Background of the Invention." The principal components of the circuit configuration 250 as shown in FIG. 4 are relatively well-known in the art and the principal structure of the configuration would be apparent to those skilled in the design of color measurement devices.

As previously described, apparatus 200 comprises a spectrophotometer apparatus for purposes of providing output data in the form of spectral characteristics of an object sample 252 under test. As shown in FIG. 4, the spectrophotometer apparatus 200 and the circuit configuration 250 include a light source unit 254 utilized for measuring the spectral response characteristics of the object sample 252. With reference to FIGS. 2 and 3, for purposes of measuring the object sample under test 252, the object sample 252 would be positioned within the shoe window 214 and centrally positioned with respect to the reference patch 213. In the particular configuration illustrated in FIG. 4, the spectrophotometer apparatus 200 is adapted to measure spectral reflection characteristics. However, it should be emphasized that a calibration arrangement in accordance with the current invention could also be utilized with apparatus adapted to measure transmittance or similar characteristics.

Various standards have been developed for spectrophotometer light source illuminants for spectral reflectance measurements in various industrial and commercial fields. For example, standards have previously been described in terms of a tungsten lamp providing an influx from a lamp operating at a Planckian distribution of 3000K. Other suggested standards have been developed by ANSI and the International Organization for Standardization ("ISO"). In addition, various CIE illuminants have also been defined, for calculations under various lighting conditions. Such light source standards are typically defined in terms of the spectral energy distribution of the illuminant. The light source 254 preferably conforms to an appropriate standard and can, for example, comprise a filament meeting a standard conventionally known in the industry as 2856K ANSI. The light source or lamp 254 is operated under control of a lamp control circuit 256, and power to the lamp control circuit 256 can be provided through a conventional power supply 258 operating under conventional AC utility power or, alternatively, batteries such as those shown as batteries 220 in FIG. 3.

Preferably, the light source 254 projects light through a collimating lens (not shown) which serves to focus the electromagnetic radiation from the light source 254 into a narrow collimated beam of light rays. Various types of conventional and well-known collimating lenses can be employed. Further, the light rays transmitted through the collimating lens would typically project through an aperture (not shown), with the dimensions of the aperture determining the size of the irradiated area of the object sample 252. Various standards have also been defined for preferable sizes of the irradiated area. Ideally, the aperture is of a size such that the irradiance is uniform over the entire irradiated area. However, in any physically realizable spectrophotometer arrangement, such uniform irradiance cannot be achieved. Current standards suggest that the size of an irradiated area should be such that irradiance measured at any point within the area is at least 90 percent of the maximum value. In addition, however, aperture size is typically limited to the size of the particular areas to be measured, and is also sized so as to reduce stray light.

The light rays emerging from the aperture (not shown) are illustrated in FIG. 4 as light rays 260 and are projected onto the irradiated area surface of the object sample 252 under test. As the light rays 260 are projected onto the object sample 252 under test, electromagnetic radiation shown as light rays 262 will be reflected from the object sample 252. As previously described in the section entitled "Background of the Invention," it is necessary to obtain quantitative measurements of this reflected light for purposes of determining the relative proportions of the light reflected from various segments of the spectrum and from various object samples. As also previously described, it is substantially impossible to measure all of the light reflected from the object sample 252. Accordingly, standard detection configurations have been developed, whereby reflected light is detected at a specific angle relative to the illumination light rays 260 projected normal to the plane of the object sample 252. More specifically, standards have been developed for detection of reflected light rays at an angle of 45° to the normal direction of the light rays 260. This angle of 45° has become a standard for reflectance measurement and is considered desirable in that this configuration will tend to maximize the range of the measurements. In addition, however, the 45° differential also represents somewhat of a relatively normal viewing configuration of a human observer (i.e., illumination at a 45° angle from the viewer's line of sight).

For purposes of providing light detection, bundled fiber optic circuits or transmission media 264 are provided. As will be explained in greater detail in subsequent paragraphs herein, light reflected from the object sample 252 is detected by a predetermined number of "segmented" detection circuits, with each circuit corresponding to a different portion of the visible light spectrum in accordance with the spectral characteristics of the particular filter associated with that detection circuit. In the circuit configuration 250 illustrated in FIG. 4, a separate fiber optic bundle 264 will be provided for each segment, although only three of the fiber optic bundles 264 are illustrated in FIG. 4. Each of the fiber optic bundles 264 provides a means for collecting and receiving the reflected light (shown as light rays 262) from the object sample 252. Although fiber optic bundles are illustrated in FIG. 4, other types of means for receiving and collecting the reflected light can be employed without departing from the principal concepts of the invention.

The light collected from the fiber optic bundles 264 is applied on symbolic paths 266 to a filtered photocell configuration 268. For each path or separate segment from a fiber optic bundle 264, a separate spectral filter is provided. As is well-known in the design of spectrophotometers, each of the filters will have a different spectral frequency response, so that the entire array of filters will provide an indication of spectral characteristics of the reflected light across the entirety of the visible light spectrum. For example, each of the filters (and associated spectral "segments") can have a bandwidth substantially in the range of 20 nanometers (nms), with each of the filters having a center frequency spaced apart approximately 20 nms from filters having adjacent frequency responses. That is, each of the filters will tend to absorb light energy at frequencies outside of the bandwidth representative of the particular spectrum portion of the filter. In this manner, with each of the filters representative of a different "segment" and different portion of the visible light spectrum, a quantitative measurement of the light reflected from the object sample and passing through each filter will provide an indication of the proportion of light reflected from the object sample within the particular frequency bandwidth of the filter. Accordingly, for a given predetermined number of filters or segments, a corresponding number of "points" can be obtained for the spectral response characteristic curve for the object sample. As previously described, a series of sixteen segments and filters, with each of the filters having a bandwidth of approximately 20 nms, can be employed. However, various other numbers of filters and various bandwidth ranges can also be employed without departing from any of the novel concepts of the invention.

It is apparent from the foregoing that the actual quantitative measurement of reflectance for a particular segment is dependent in substantial part on the spectral transmittance characteristics of the filters. Accordingly, various well-known standards have been developed with respect to spectral characteristics of color measurement device filters. For example, with respect to densitometer apparatus, standards were previously described for the prior art densitometer apparatus 100 illustrated in FIG. 1. Again, a variable number of filters and segments, with corresponding varying bandwidths, can be employ with the spectrophotometer apparatus 200 in accordance with the invention.

Continuing to refer to the filtered photocell configuration 268, the configuration 268 can comprise a series of cells such as photovoltaic sensor cells (not specifically shown outside of the configuration 268). A sensor cell would be positioned essentially behind each of the filters, so that the light rays passing through the filters would impinge on receptor surfaces of the sensor cells. Accordingly, the configuration 268 would comprise a separate sensor cell associated with each of the separate filters. Such sensor cells can comprise conventional photoelectric elements adapted to detect the light rays emanating through the corresponding spectral filters. The sensors are well-known in the art of color measuring device design, and are preferably adapted to generate electrical currents having magnitudes proportional to the intensities of the sensed light rays. Various types of commercially available sensors can be employed with the photocell configuration 268.

The magnitude of the electrical current comprising an output signal for each of the filters will be proportional to the intensity of the reflected light rays transmitted through the corresponding spectral filter. These light rays will have a spectral distribution corresponding in part to the product of the spectral reflectance curve of the object sample 252 under test, and the spectral response curve of the corresponding filter. Accordingly, for a particular segment of the visible light spectrum represented by the spectral response curve of the filter, the magnitude of the electrical current represents a quantitative measurement of the proportion of reflectance of the object sample 252 within the frequency spectrum for which the filter readily passes visible light.

Continuing to refer to FIG. 4, the electrical currents representative of the proportion of light passing through the filters of the photocell configuration 268 are applied on transmission lines of line group 270. For purposes of simplification and understanding, the line group 270 is illustrated in FIG. 4 as comprising a single directional line. However, in the physically realized circuit configuration 250, the line group 270 would comprise a separate line pair for each of the frequency segments and, correspondingly, for each of the filters and photocells of the configuration 268. That is, a line pair would be interconnected to each of the photocells of the configuration 268.

As further shown in FIG. 4, each of the electrical current signals appearing on pairs of the line group 270 are applied as input signals to a series of linear amplifier circuits 272. Again, for purposes of simplification and understanding, the linear amplifier circuitry 272 is illustrated in FIG. 4 as comprising a single symbolic element. However, the linear amplifier circuitry 272 would preferably comprise a separate linear amplifier for each of the segments of the spectrophotometer apparatus 200, with each line pair of the line group 270 interconnected to a separate one of the linear amplifiers of circuitry 272. The linear amplifiers of the circuitry 272 can be conventional in structure and function, and responsive to the electrical current output signals of the associated photocell sensors to provide a means for converting low level output current from the respective sensor on the corresponding input line pair to a voltage level signal generated as an output signal for each linear amplifier. The voltage level of the output signal of each linear amplifier is preferably of a magnitude suitable for subsequent analog-to-digital (A/D) conversion functions. Such amplifiers are well-known in the circuit design art and are commercially available with an appropriate volts per ampere conversion ratio, bandwidth and output voltage range. The voltage output signal from each of the linear amplifiers is applied as an output signal to separate ones of the line group 274.

The spectrophotometer apparatus 200 also includes a single side sensor 276 which is utilized to compensate for changes in lamp intensity of the source light 254 in accordance with the invention as described in subsequent paragraphs herein. The side sensor 276 can comprise an appropriate photovoltaic sensor cell or similar sensor responsive to the light rays 278 emanating from the source light 254. In known arrangements employing side sensors for lamp compensation, the spectral response characteristics of the side sensors are "matched" to the spectral response characteristics of the particular detection channel or segment then being compensated. For example, in various densitometer arrangements, wherein cyan, magenta and yellow color channels may be employed, it is known to provide for matching the spectral response characteristic of the side sensor to the particular channel then being compensated. Such a matching arrangement may be achieved through the use of multiple side sensors each having a filter with a spectral response characteristic matching that of one of the channels of the densitometer or, alternatively, a single side sensor may be employed with a series of filters which are individually and sequentially "moved" into appropriate position so as to provide a response characteristic matching that of the then currently evaluated color channel. Similar arrangements have been employed in other color measuring devices, such as spectrophotometers.

In contrast, and in accordance with the invention, the side sensor 276 employed in the spectrophotometer apparatus 200 does not include any "changing" of spectral response characteristics (e.g. by sequential movement of independent filters into positions adjacent the side sensor), and further does not include any components to necessarily match the spectral response characteristics of the side sensor 276 with spectral response characteristics of a segment then being evaluated. If desired, the side sensor 276 can include an appropriate filter for filtering out stray light and providing passage of the light rays 278 only within a bandwidth "representative" of the lamp intensity of the source light 254. Of primary importance is the concept that the calibration arrangement subsequently described herein does not require any matching of the side sensor spectral response with the spectral response characteristics of the individual segments. As further described in subsequent paragraphs herein, the calibration procedure utilized in accordance with the invention includes the determination of a compensation coefficient (for each segment) which is indicative of the relationship between changes in the lamp intensity detected by the side sensor and changes in the reflectance intensity detected by filters of the individual segments as the lamp changes in intensity.

The electrical current output signal from the side sensor 276 generated on line pair 280 is applied as an input signal to the linear amplifier circuit 282. The linear amplifier circuit 282 can preferably comprise a single linear amplifier having structure and function similar to the linear amplifiers of the circuitry 272. That is, the linear amplifier 282 can generate an appropriate voltage level output signal on line 284 proportional to the electrical current input signal on line 280. As further shown in FIG. 4, appropriate supply voltage can be applied to the linear amplifier circuitry 272 and linear amplifier circuit 282 from the supply voltage circuit 286 by means of transmission line 288.

Each of the voltage signal outputs from the linear amplifier circuitry 272 and 282 are applied as input signals from lines 274 and 284 to multiplexer circuitry 290. Again, it should be noted that the line group 274 will include separate lines for each spectrum segment of the spectrophotometer apparatus 200. The multiplexer circuitry 290 can be conventional in design and comprise a series of one or more conventional multiplexers. The multiplexer circuitry 290 operates so as to time multiplex the output signals from the linear amplifier circuitry (including circuitry 272 and linear amplifier 282) onto the conductive path 292. Timing for operation of the multiplexer circuitry 290 can be provided by means of clock and similar signals from the processor 294 via path 296. Operation of the processor 294 will be described in greater detail in subsequent paragraphs herein. Again, the structure and function of the multiplexer circuitry 290 is relatively conventional in design. During actual measurements of the reflectance from the object sample 252, the spectrophotometer apparatus 200 will utilize the resultant multiplexed signals on path 292 as sequentially representative reflectance signals from each of the spectrum segments and each of the linear amplifiers of the linear amplifier circuitry 272, and will also represent a voltage output signal corresponding to the lamp intensity signal from the linear amplifier 282.

The resultant multiplexed signals from the multiplexer circuitry 290 are applied as output signals on the conductive path or paths 292. The resultant multiplexed signals are further applied as input signals to a relatively conventional analog-to-digital (A/D) converter circuit 298. The A/D converter 298 comprises a means for converting the analog multiplexed signals on the conductive paths 292 to digital signals for purposes of subsequent processing by the processor 294. The A/D converter 298 can be conventional in design and may be controlled by timing and similar pulse signals applied as input signals on conductive path 300 from the processor 294. Supply voltage for the A/D converter 298 can be provided by the supply voltage circuit 286 over conductive paths 304. Similarly, the supply voltage circuit 286 can also supply appropriate voltage level signals to the multiplexer circuitry 290 over the conductive paths 306.

As further illustrated in FIG. 4, the digital output signals from the A/D converter circuit 298 are applied as input signals on transmission line 302 to the processor 294. The processor 294 is utilized for control of various functions associated with the spectrophotometer apparatus 200, including calibration methods in accordance with the invention as described in subsequent paragraphs herein. Numerous types of conventional and commercially available processors can be employed for the processor unit 294. An exemplary processor could, for example, comprise the Intel 80C31 8-byte CMOS microcomputer commercially available from the Intel Corporation.

Figure 5:
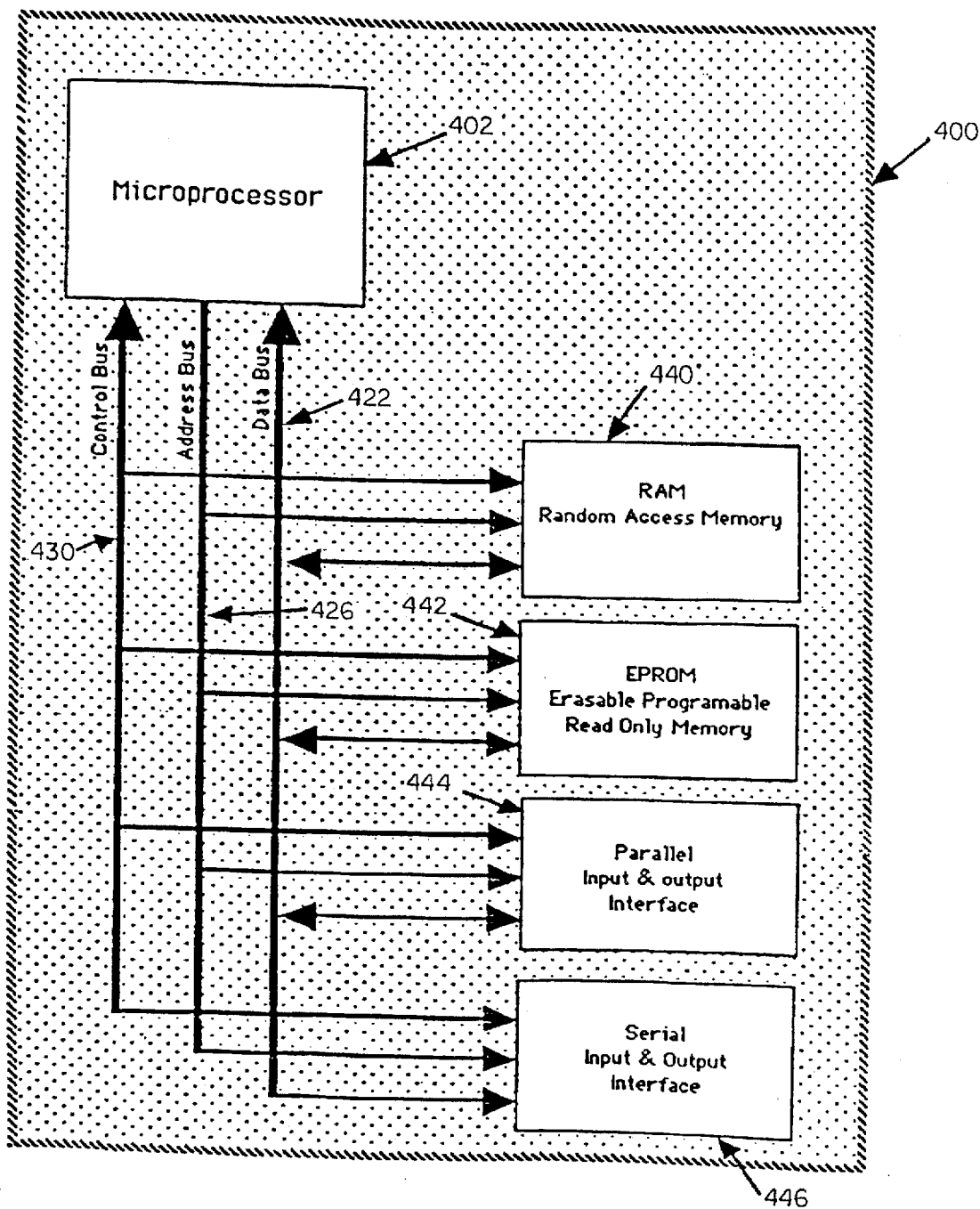
FIG. 5 is a diagram of an exemplary digital processing arrangement.
Figure 6:
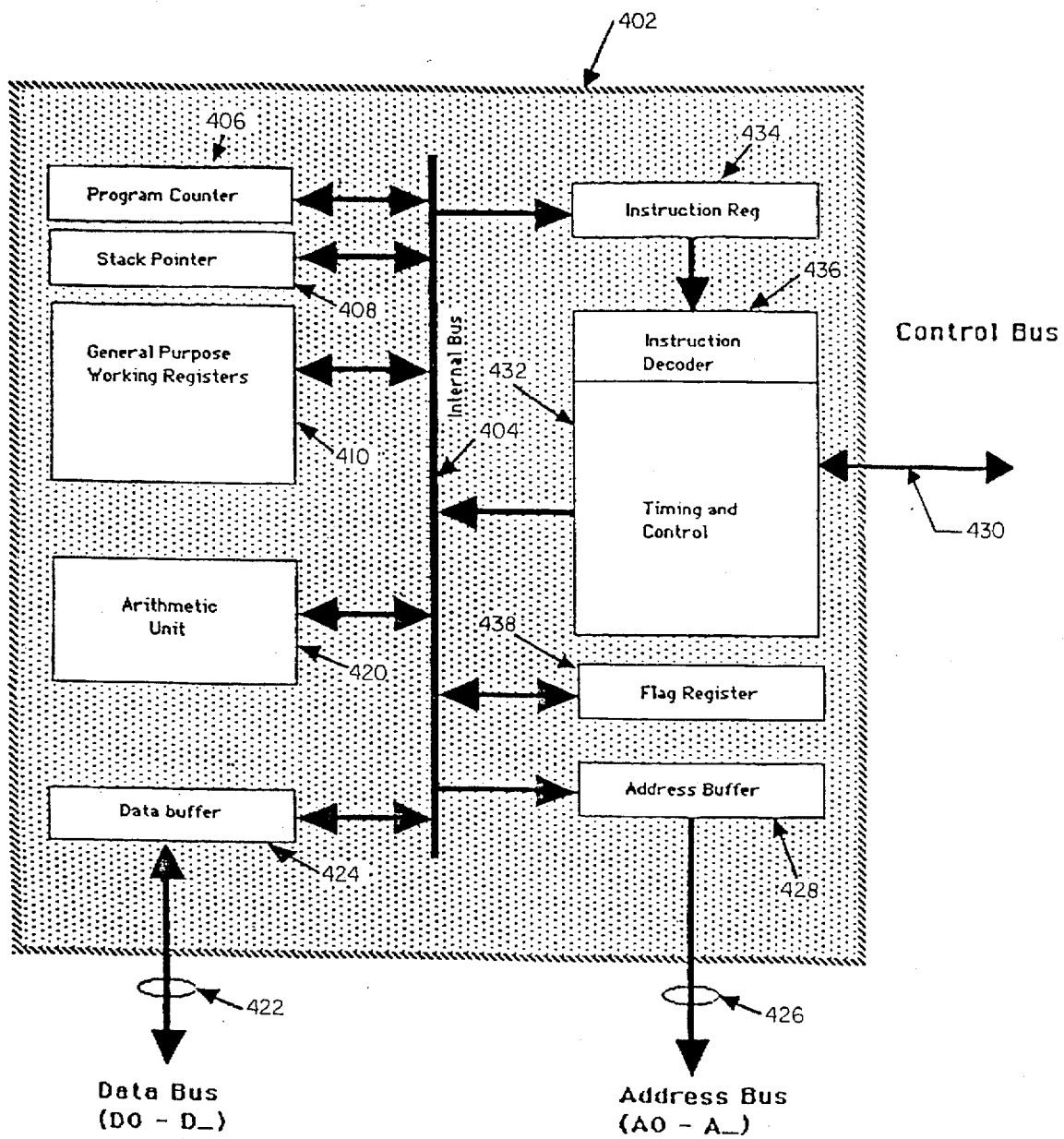
FIG. 6 is a diagram of an exemplary processor configuration.

For purposes of general background, FIGS. 5 and 6 illustrate a general structural diagram of a computer configuration with generalized components. The arrangement shown in FIGS. 5 and 6 does not necessarily correspond specifically to the processor and associated component configuration illustrated in FIG. 4. Instead, FIGS. 5 and 6 are merely for purposes of background description of a generalized form of a programmable device. Referring specifically to FIG. 5, a generalized processing unit 400 is illustrated. As shown therein, the processing unit 400 can comprise a relatively conventional microprocessor 402. As previously described, although various types of well known and commercially available devices can be employed for the processor 402, a typical internal configuration for processor 402 is illustrated in FIG. 6, and a brief and simplistic description thereof will be provided.

Referring specifically to FIG. 6, the processor 402 comprises an internal bus 404 which provides a means for bidirectional communication between conventional circuit components of the processor 402. For example, signals can be transmitted to and received from the program counter 406, which comprise signals representative of the "next" instruction in the computer memory to be executed. Communication can also be provided between the internal bus 404 and processor components such as the stack pointer 408, general purpose registers 410 and arithmetic unit 420. Each of these processor components is well known to those skilled in the art of internal computer system design.

The transmission and reception of data from memories and other components of the processing unit 400 can be provided by the data bus 422 which is connected to the internal bus 404 through a conventional data buffer 424 so as to provide bidirectional communication therewith in the form of multi-digit parallel binary signals. The internal bus 404 is also connected to an address bus 426 through an address buffer 428. The processor 402 can provide, for example, multi-digit parallel binary address signals on the bus 426 for directed communication between the processor 402 and the various memories and other devices having signal communications through the data bus 422.

Conventional system control is provided by interconnection of the control bus 430 to timing and control circuitry 432. Communication signals from the conventional timing and control circuitry 432 can be applied to various components of the processor 402 through the internal bus 404.

The processor 402 also includes other conventional circuit components, including an instruction register 434. The instruction register 434 comprises a register to which the "next" instruction is stored for purposes of decoding an execution. The data within the instruction register 434 is applied to the instruction decoder 436 which comprises conventional circuitry for decoding the instruction data received from the next program location in memory. The processor 402 can also include such conventional components as a flag register 438 utilized for various programming control within the processor 402.

The control bus 430 can be characterized as comprising a series of individual command signal leads. The signal leads can include "transmitted" commands such as "read," "write," "memory" and "I/O" commands. In addition, the control bus 430 can be adapted to apply certain "received" commands to the timing and control circuitry 432. Such commands can include "wait," "reset" and "interrupt" commands. The use of these commands is well known in the field of computer system design. For example, if data is to be read from a certain address location in a memory of the processing unit 400, "enable" signals can be applied to the "read" and "memory" command leads from the timing and control circuitry 432. Correspondingly, the address of the particular memory location to be read can be transmitted on an address bus 426, while the data to be read from the particular memory location will be applied to the processor 402 on data bus 422. Similarly, when data is to be applied to a particular I/O device associated with the processing unit 400, "enable" signals can be applied on the "write" and "I/O" signal command leads from the timing and control circuitry 432. Correspondingly, the address designation of the I/O device can be applied on address bus 426, while the particular data to be transmitted to the I/O device can be applied on data bus 422. Again, the circuitry associated with processor 402, and processor 402 itself are well known in the art.

Returning again to FIG. 5, the processing unit 400 includes memory storage elements such as the random access memory (RAM) 440. The RAM 440 is conventional in design and includes memory locations wherein data may be stored and modified during execution of program sequences. Similarly, for storage of "permanent" data or instructions wherein modifications must be made only occasionally, a conventional erasable-programmable read only memory (EPROM) 442 is also employed. Both the RAM memory 440 and the EPROM memory 442 are interconnected with the processor 402 so as to allow control and address location signals to be applied on the control bus 430 and address bus 426, respectively. In addition, for purposes of reading data from the memories into the processor 402, and for writing data into the memories, bidirectional communication is established between the RAM memory 440, EPROM memory 442 and the processor 402 through data bus 422.

For purposes of intercommunication with external devices, the processing unit 400 can also include a parallel I/O interface module 444 and a serial I/O interface module 446. The parallel interface module 444 provides a means for transmitting and receiving data signals between the processor 402 and external devices which generate and receive signals in parallel format. The serial interface module 446 is utilized to interface with external devices in a serial format.

Like the RAM memory 440 and the EPROM memory 442, the interface modules 444 and 446 are interconnected to the processor 402 through the control bus 430 and address bus 426 for purposes of applying control and address information data signals, respectively, to each of the modules. In addition, the interface modules 444 and 446 are interconnected to the processor 402 through data bus 422 so that data signals are bidirectionally transferrable between the modules 444, 446 and processor 402. It should be emphasized that the general circuitry of the processing unit 400 and the functional operations associated therewith are well known in the field of computer system design.

The aforedescribed processor configuration as illustrated in FIGS. 5 and 6 is merely exemplary of certain of the general concepts associated with processor and associated component design. In the particular embodiment illustrated in FIG. 4, the processor is illustrated as a separate processing unit 294 independent of the memory and similar elements. As further shown in FIG. 4, the processor 294 can provide control signals to both the supply voltage circuitry 286 and lamp control circuitry 256 via transmission paths 308 and 310, respectively. Control signals can also be applied from the processor 294 to the power supply circuit 258 via path 312. In addition, such control signals can be applied to reset circuitry 314 which, in turn, can also apply, as input signals to the processor 294, reset signals via path 316. Although FIG. 4 further illustrates other interconnections among components such as the power supply circuitry 258 and reset circuitry 314, the structure and function of such interconnections will be apparent from the illustration of FIG. 4 and other detailed descriptions set forth herein.

The spectrophotometer apparatus 200 can also comprise a conventional address decoder 320 interconnected to the address bus of the bus configuration 322 for the processor 294. The address decoder 320 is utilized to decode the address range for the various devices associated with the bus configuration 322. Such an address decoder configuration is convention in design.

The apparatus 200 can also include a conventional EPROM 324 which can comprise, for example, a CMOS 512K EPROM. In addition, the spectrophotometer apparatus 200 can also comprise a random access memory (RAM) 326. The RAM 326 can, for example, comprise an 8192 byte static random access memory.

As previously described, the spectrophotometer apparatus 200 can also include a series of keys 243. These keys 243 provide a means for manual input of data by the spectrophotometer operator. Still further, the apparatus 200 further includes the display 240 for purposes of providing data display to the operator. In association with the aforedescribed components which are directly or indirectly connected to the bus configuration 322 of the processor 294, conventional latching circuitry 326 is also employed for purposes of latching data applied to and from the bus configuration 322.

As further shown in FIG. 4, the processor 294 is interconnected to a conventional RS232 I/O interface circuit 328. The interface circuit 328 provides an interface to an external computer or printer device 330, for purposes of transmitting and receiving data to and from the interface device, respectively. Control signals from the processor 294 to the interface 328 can be applied via path 332. Correspondingly, data from the processor 294 can be applied as input data through the interface 328 via transmission path 334. Correspondingly, data from the computer printer device 330 can be applied through the interface 328 and input to the processor 294 by means of transmission path 336.

The foregoing provides a brief description of various of the components of the circuit configuration 250 of the spectrophotometer apparatus 200. Many of these components are also utilized in various other types of color measurement apparatus. For example, a detailed description of similar components for use in a densitometer are described in detail in the commonly assigned and currently pending U.S. patent application Ser. No. 480,331 filed Feb. 13, 1990, which is a continuation of commonly assigned U.S. patent application Ser. No. 309,342 filed Feb. 10, 1989, now abandoned. Concepts associated with the use of a color measurement device and an interface for communication with external devices are disclosed in the commonly assigned Peterson et al U.S. Pat. No. 4,591,978, issued May 27, 1986.

In brief summary, the apparatus 200 is adapted to operate as an automated instrument for providing a spectral reflectance analysis of object samples. When the object sample is positioned appropriately in the spectrophotometer apparatus 200, light from the source 254 is projected onto the surface 252 of the sample, and reflected light rays 262 are received by the fiber optic bundles 264. A separate fiber optic bundle 264 is provided for each spectral segment to be analyzed by the apparatus 200. The light rays passing through the fiber optic bundles 264 are applied to a configuration of filters and photocells 268. Each of the filters will substantially pass the reflected light only within the bandwidth corresponding to the particular segment. Electrical current signals generated from the photocells of the configuration 268 are applied to linear amplifier circuitry 272, and voltage output signals are generated therefrom. Correspondingly, the intensity of the light rays 278 from the light source 254 is detected by the side sensor circuit 276. Electrical current signals representative of this intensity are applied as input signals to the linear amplifier 282, and a corresponding voltage level output signal is generated therefrom.

The voltage signals from the linear amplifier circuitry 272 and 282 are applied as input signals to the multiplexer circuits 290. The multiplexer circuits 290 provide time multiplexed signals which are applied as input signals to the A/D converter 298. The converter 298 converts the analog signals to appropriate digital signals, and applies the same to the processor 294. The processor 294 can be utilized to perform appropriate computations and measurements of the digital signals from path 302 so as to generate data indicative of the spectral reflectance characteristics of the object sample 252 for each of the spectral segments. As desired, this data can be visually displayed to an operator through the display 240. Correspondingly, such data can be applied to the external devices 330 through the interface 328. Control of the processor 294 can be provided, at least in part, through operator input from the keys 243. The general operation of spectrophotometers, given spectral data from a series of segments, is relatively well known in the art.

In accordance with the invention, and as previously described in part, it is desirable to "calibrate" the spectrophotometer apparatus 200. In part, this calibration is provided for purposes of compensating for changes in lamp temperature and intensity. A calibration or lamp compensation arrangement in accordance with the invention will now be described in the following paragraphs. This compensation arrangement is also illustrated as a series of sequence diagrams in FIGS. 7, 8 and 9. The actual functions performed with respect to various computations and similar procedures are preferably performed by computer software operating with the processor 294.

For purposes of calibration and lamp compensation, a reference sample is utilized by the operator, in place of an actual object sample to be tested. However, the principal operations of the spectrophotometer apparatus circuit configuration 250 illustrated in FIG. 4 are essentially substantially the same, with a reference sample replacing the conventional object sample under test. That is, the operation of the various optics circuitry for obtaining spectral reflectance characteristics is performed as previously described.

For purposes of calibration and lamp compensation, a reference sample can be provided by the apparatus manufacturer, along with the specific apparatus itself. The reference sample can include, for example, a "white spot" reference. With the white spot reference, reflectance data comprising actual data for the white spot measured at the manufacturer's facilities can also be provided to the operator. Such data will be referred to in subsequent paragraphs herein as the "desired" reflectance data. Such data would be in the form of, for example, reflectance percentages for each of the spectral segments. This data provides a basis for relating voltage signal levels to reflectance percentages for the particular instrument. That is, without such data representing previously measured reflectances, the initial relationship of signal levels to reflectances for this particular instrument would be unknown. In addition to providing printed information describing the desired reflectance data for the operator, such data can also be prestored by the apparatus manufacturer within appropriate memories of the processor 294.

For purposes of performing the calibration and lamp compensation methods in accordance with the invention, the reference sample comprising the "white spot" reference can be placed in the spectrophotometer apparatus 200 as previously described with respect to FIGS. 2 and 3. Thereafter, the operator can "select" the calibration procedures to be performed by appropriate input of data via the keys 243. When the operator enters the appropriate data through the keys 243, the processor 294 and associated components will recognize that the calibration procedure is to be performed, and various initialization procedures (clearing of memories, etc.) can be executed. Following such initialization, various automatic calibration procedures can be performed with respect to errors which may be caused by allowed tolerances of the various electronics of the circuit configuration 250. Such calibration procedures are relatively well known in the color measurement arts, and do not form any of the principal concepts of the present invention. That is, such calibration procedures are substantially separate and distinct from the calibration and lamp compensation procedures in accordance with the present invention.

For purposes of performing the lamp compensation procedures, the circuit configuration 250 will utilize the desired reflectance data for the reference sample. As previously described, such desired reflectance data can be entered by the operator at the time of performance of the lamp compensation procedures or, alternatively, can comprise prestored data then currently stored in appropriate memories of the circuit configuration 250. Accordingly, the processor 294 can contain appropriate software to "prompt" the operator (through signals provided via the display 240) as to whether such prestored desired reflectance data should be utilized or, alternatively, whether the operator wishes to enter desired reflectance data.

Figure 7:
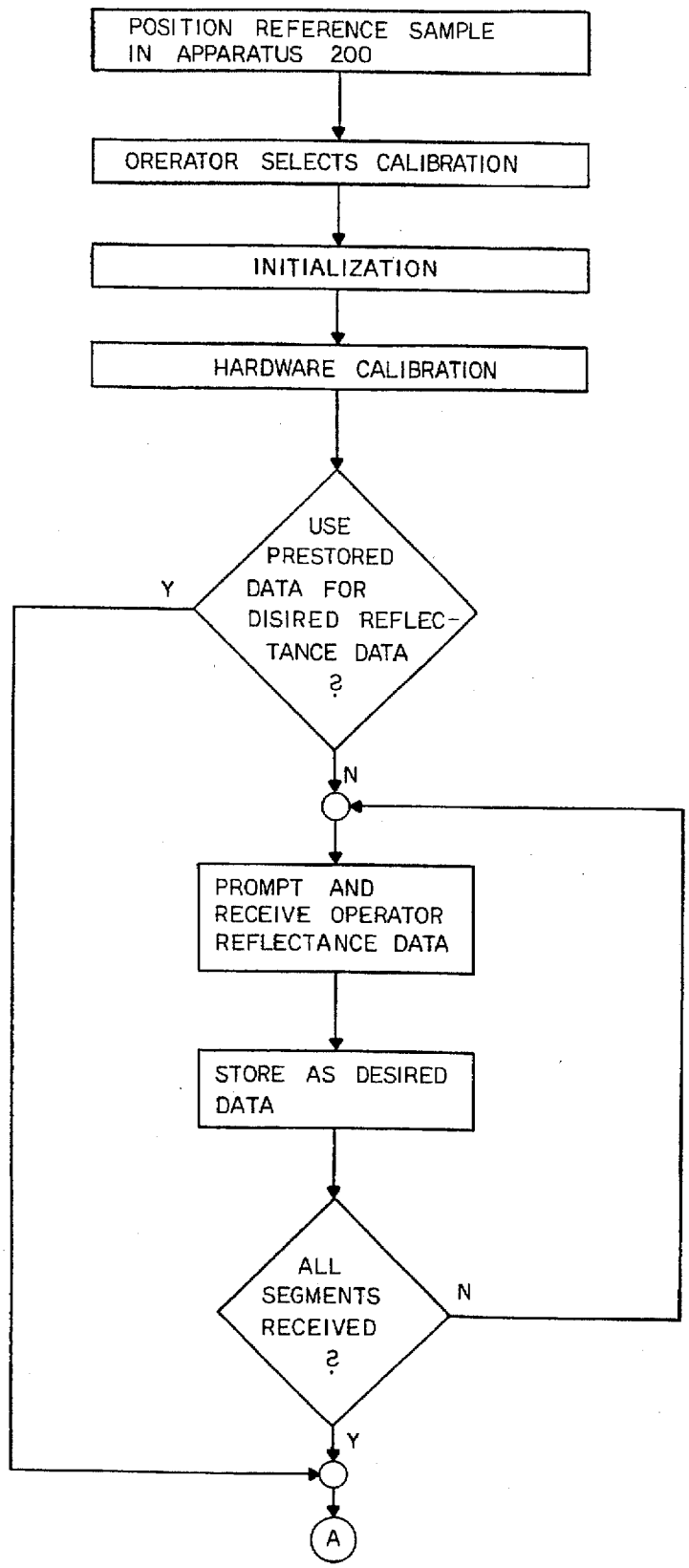
FIG. 7 represents a functional sequence diagram for performance of certain initial calibration procedures in accordance with the invention.

As shown in FIG. 7, if the operator wishes to enter the desired reflectance data, the apparatus 250 can be adapted to prompt the operator (again through signals applied to the display 240) for the operator to enter the desired reflection data through the keys 243.

For purposes of subsequent description herein, the letter notation "$\underline{x}$" will represent a selected spectral segment for the various measurements to be performed by the apparatus 200. Correspondingly, the letter notation "$\underline{a}$" will represent a present or current measurement of a sequence of measurements to be performed as described herein.

With these notations, for purposes of describing the desired reflectance data, the notation WRx will represent the value of the desired reflectance data for spectral segment $\underline{x}$, whether such data is in the form of prestored data or data then entered by the operator. As the operator enters the desired reflectance data, such data is stored and a determination is made as to whether data for all spectral segments has been received. If not, the apparatus 200 can continue to prompt the operator for additional reflectance data until data representative of all segments is stored in the appropriate memories of processor 294. Correspondingly, it is apparent that the processor 294 can be programmed so that the operator can enter desired reflectance data only for a subset of the entirety of the segments, with the desired reflectance data for the other segments corresponding to prestored data.

After the desired reflectance data for all segments has been stored within appropriate memories of the processor 294, a determination can be made as to the elapsed time since a prior measurement has been performed by the apparatus 200. A primary purpose for this determination is that a first measurement to be performed by the apparatus 200 is to be essentially characterized as a "cold lamp" measurement. Accordingly, if insufficient time has elapsed since the lamp of the light source 254 has previously been activated, the first measurement to be taken during the lamp compensation procedure may occur prior to the time that the lamp "cooled" sufficiently since a previous measurement. If insufficient time has elapsed since a last measurement utilizing the lamp of the source 254, the apparatus 200 can provide an automated delay before a first measurement is performed. The actual elapsed time for such delay should be sufficient so as to assure that a first reading is performed with a "cold lamp", and a warm up characteristic can be obtained through the lamp compensation measurements.

When sufficient time has elapsed since the last measurement, a first reading of the reflectance sensor values for each of the segments can be obtained, in accordance with the reflectance measurement procedures previously described with respect to the circuit configuration 250 illustrated in FIG. 4. Correspondingly, a first reading is also obtained of the intensity measurement of the lamp of light source 254 through the side sensor 276. Data representative of the reflectance sensor measurement values for each segment, and data representative of the side sensor measurement value can then be stored in appropriate memories of the processor 294.

Figure 8:
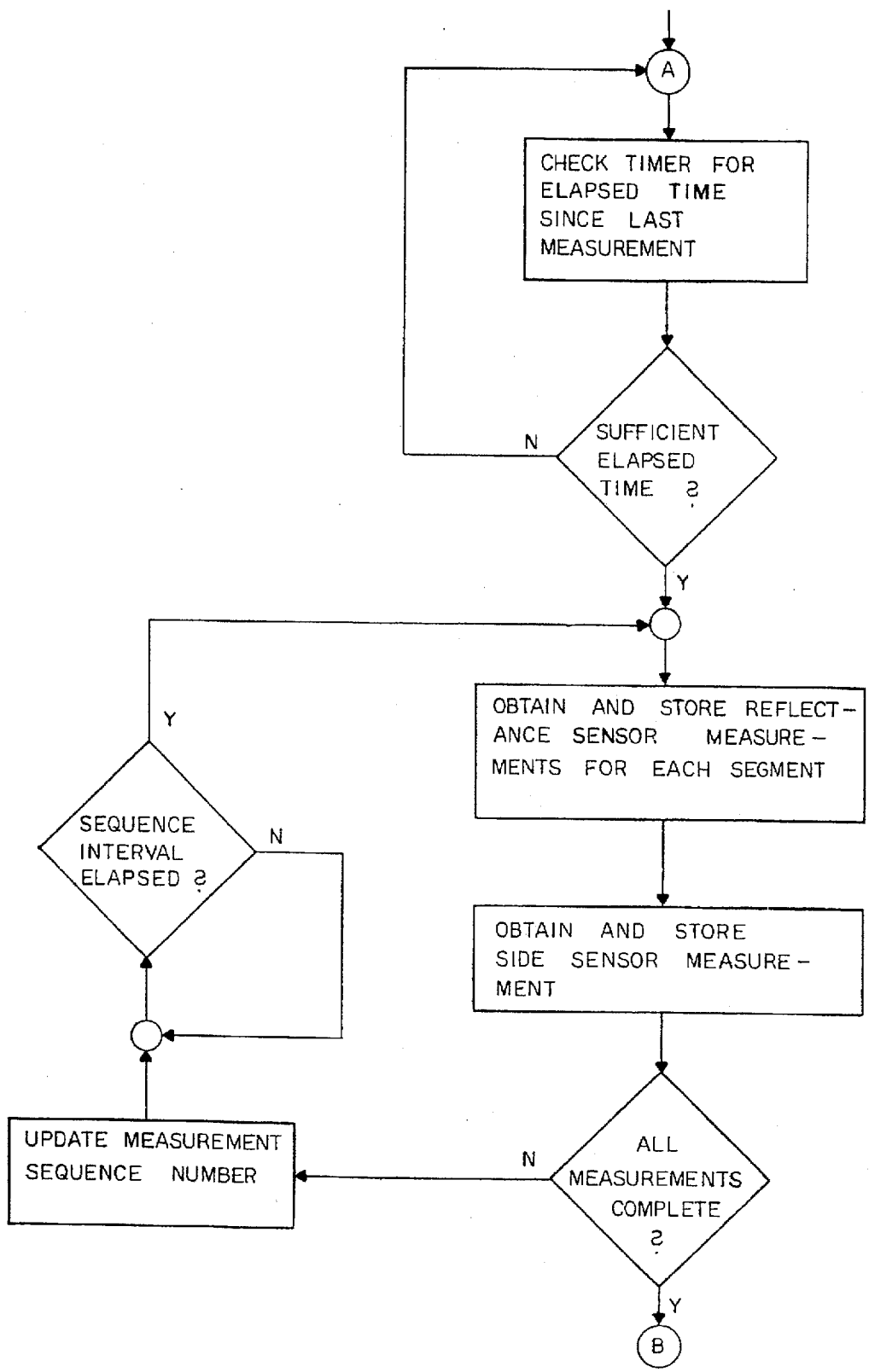
FIG. 8 represents a further functional sequence diagram for performance of calibration procedures in accordance with the invention, and particularly showing functions associated with reflectance sensor and side sensor measurements.
Figure 9:
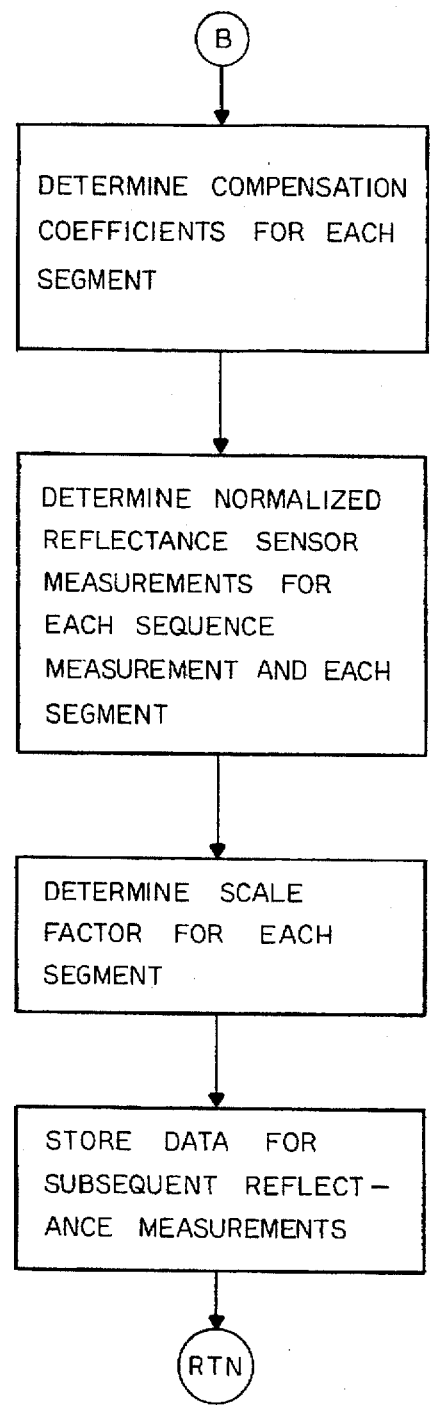
FIG. 9 represents a still further functional sequence diagram for performance of certain calibration procedures in accordance with the invention, and particularly showing the determination of various calibration and compensation parameters of the procedures.

Following the first reading, and in accordance with the invention, a plurality of additional readings of the reflectance sensor measurement values and side sensor measurement values can be performed, as the lamp of the light source 254 begins to "heat up." In this regard, and in accordance with the invention, the calibration and lamp compensation procedure comprises, in part, a timed sequence of reflectance sensor measurements and side sensor measurements. Therefore, and as shown in FIG. 8, following such measurements, a determination can be made as to whether the appropriate number of measurements have been completed. If not, an appropriate measurement sequence number can be updated. In addition, and in accordance to the invention, the measurements are obtained at predetermined time intervals. Accordingly, the circuit configuration 250 can be adapted to determine if the appropriate sequence interval time has elapsed. If not, a delay will occur and a determination of whether the sequence interval time has elapsed can be periodically executed. When the appropriate sequence interval time has elapsed, and assuming that all measurements have not been completed, a new set of reflectance sensor measurement values and side sensor measurement value can be obtained and stored in appropriate memory. For purposes of description, the side sensor measurement values are referred to in subsequent paragraphs herein as values SS1, SS2, ... SSN, where N represents the total number of measurements to be performed within the lamp compensation sequence. Correspondingly, the reflectance sensor measurement values for a particular segment $\underline{x}$ are referred to herein as reflectance sensor measurement values RS1x, RS2x, ... RSNx, where N again represents the total number of measurements within the measurement sequence.

The lamp compensation procedure in accordance with the invention is not limited to a particular number of measurements N or a particular timed sequence interval between measurements. However, the number of measurements and the sequence interval should be sufficient so that a "warm-up" characteristic is obtained with respect to the light source 254. For example, experimentation has shown that a series of five measurements may be utilized, with the measurements spaced at intervals of approximately three seconds.

Following the measurements of the side sensor values and the reflectance sensor values, the circuit configuration 250 can be adapted to determine a filter compensation coefficient for each segment. With the filter compensation coefficient for a segment $\underline{x}$ referred to as coefficient CCx, the coefficient can be determined in accordance with the following:

$$CCx=((RS1x/RSNx)-1)/((SS1/SSN)-1) \qquad \text{(Equation 2)}$$

where RS1x represents the reflectance sensor measurement value for the first measurement for segment $\underline{x}$, RSNx represents the reflectance sensor measurement value for the last measurement for segment $\underline{x}$, SS1 represents the side sensor measurement value for the first measurement, and SSN represents the side sensor measurement value for the last measurement. Again, the filter compensation coefficient is a compensation value which is provided separate and independent for each spectral segment.

To further explain the concept of the compensation coefficients, reference is made to earlier description relating to the structural configuration of the side sensor 276 illustrated in FIG. 4. As previously described, one of the concepts of the invention is the lack of any necessity of matching the spectral response characteristics of the side sensor to the spectral response characteristics of individual segments. Prior art system employing side sensors would typically utilize multiple side sensors with filters having differing response characteristics matching response characteristics of the detection channels or segments, or would otherwise utilize a single side sensor with multiple filters which could be "moved" into position adjacent the side sensor for providing differing response characteristics matching the channels or segments. As earlier described, and in accordance with the invention, the side sensor 276 can employ a fixed spectral response, with the spectral response not necessarily being of the same characteristic as any given segment. With a change in intensity of the lamp of the light source 254, a corresponding change will be detected by the side sensor. Further, however, a corresponding change in reflection intensity will also occur with respect to each of the segments. It is the determination of the compensation coefficient which provides an indication of the relationship between the change in the side sensor detected intensity and the change in reflection intensity detected by a segment as the lamp correspondingly changes in intensity. That is, the compensation coefficient for a given segment represents a ratio of change in the reflectance sensor measurement to a change in the side sensor measurement. By utilizing the compensation coefficients for calibration as described in subsequent paragraphs herein, spectrophotometers in accordance with the invention avoid the expense and circuit complexity of requiring multiple sensors with differing spectral response characteristics or individual side sensors requiring movable filters or the like to adjust the side sensor response characteristics.

Following the determination of the filter compensation coefficients, the previously stored reflectance sensor measurement values can be normalized. With a normalized reflectance sensor measurement value referred to as RScxa, where $x$ represents the particular spectral segment and $a$ represents the current measurement, these normalized reflectance measurement values can be determined in accordance with the following:

$$RScxa=RSxa[(((SS1/SSa)-1)CCx)+1] \qquad \text{(Equation 3)}$$

where RSxa represents the reflectance sensor measurement value for segment $x$ and measurement $a$, SS1 represents the side sensor measurement value for the first reading, SSa represents the side sensor measurement value for the current measurement, and CCx represents the filter compensation coefficient for the current spectral segment. The normalized reflectance measurements essentially represent compensation of the reflectance sensor measurements for changes in side sensor measurements which are adjusted by known differences in their drifts.

Using the normalized reflectance sensor measurement values, a scale value can then be determined for each segment. This scale value, referred to herein as WSx for segment $x$, essentially represents the conversion of a measured reflectance quantity to a percentage reflectance for the segment. That is, the scale factor conversion provides a value representative of the portion (as a percentage) of source light which is reflected from the sample, for the portion of the spectrum represented by the segment and corresponding filter. This value can be characterized as the filter reflectance or the reflectance for the particular segment. A scale value for each of the spectral segments can be determined in accordance with the following:

$$WSx=[(RSc1x+RSc2x+\ldots RScNx)/N]/WRx \qquad \text{(Equation 4)}$$

where RSc1x represents the normalized reflectance sensor measurement value for the first measurement reading and for the current segment $x$, RSc2x represents the normalized reflectance sensor measurement value for the second measurement reading and for segment $x$, and RScNx represents the normalized reflectance sensor measurement value for measurement reading N and segment $x$. Also, WRx represents the desired reflectance value previously stored for segment $x$.

In accordance with the foregoing, a compensation arrangement is provided whereby a series of readings are obtained, including a "cold" lamp reading. Reflectance readings thereafter within the timed sequence are essentially normalized back to the first reading. With the determination of the filter compensation coefficient, the normalized reflectance sensor measurement values and the scale value, appropriate and sufficient data is obtained for purposes of subsequent compensation of actual reflectance sensor measurement values obtained from object samples under test. More specifically, the compensated reflectance measurement value for an object sample under test, and for segment $x$, can be referred to as Rx. This compensated reflectance value can be determined in accordance with the following:

$$Rx=WSx[RSx((CCx((SS1/SS)-1))+1)] \qquad \text{(Equation 5)}$$

where WSx represents the scale factor for segment $x$, RSx represents the actual measured reflectance sensor value for segment $x$, CCx represents the filter compensation coefficient for segment $x$, SS1 represents the side sensor measurement value for the first reading obtained during the lamp compensation procedure, and SS represents the side sensor measurement value obtained during the current measurement. In this manner, a compensation arrangement is obtained for compensating for various lamp characteristics.

In accordance with another aspect of a lamp compensation arrangement in accordance with the invention, it is also possible to include compensation for temperature. That is, a long-term temperature coefficient can be applied to each of the spectral segments and to the side sensor.

For purposes of describing the temperature compensation arrangement in accordance with the invention, reference is again made to Equation 5, where an actual reflectance sensor measurement for segment $x$ is shown as RSx. To provide for temperature compensation in accordance with the invention, the quantity RSx can be replaced within Equation 5 by the following:

$$RSx \rightarrow RSx(1+(Kx*Tc)) \qquad \text{(Equation 6)}$$

where Kx represents a temperature coefficient determined for segment $x$, and Tc represents the difference between a temperature measured during the first lamp compensation calibration reading and a present temperature reading. The temperature coefficient Kx essentially represents the concept that for a given change in temperature, the reflectance sensor will correspondingly change by a certain percentage. To provide for the temperature compensation as shown in Equation 6, the circuit configuration 250 illustrated in FIG. 4 can include conventional means for determining temperatures occurring at various reference sample readings and object sample readings.

To provide for further temperature compensation, a compensation arrangement can also be provided for the side sensor measurement. Referring again to Equation 5, the side sensor measurement value obtained during the then-current measurement is shown as reading SS. For purposes of providing for temperature compensation, the term SS within Equation 5 can be replaced in accordance with the following:

$$SS \rightarrow SS(1+(Ks*Tc)) \qquad \text{(Equation 7)}$$

where Ks represents a temperature coefficient obtained for the side sensor, and Tc again represents the difference between the temperature measured during the first calibration reading, and the present reading. Such temperature coefficients can be obtained through use of external test equipment.

In accordance with the foregoing, the spectrophotometer apparatus 200 can be utilized for performance of determining spectral response characteristics of object samples under test. In addition, and in accordance with the invention, the spectrophotometer apparatus 200 can include apparatus and methods for performance of various calibration and lamp compensation procedures. However, it should be emphasized that the principles of the calibration and lamp compensation procedures are not limited to the specific spectrophotometer apparatus 200 described herein. In fact, the procedures can be employed with apparatus other than spectrophotometers. Still further, the features of the calibration and lamp compensation procedures described herein and in accordance with the invention are not in any manner necessarily limited to a specific number of spectral segments or the like. A different number of segments and filters having various bandwidths can be employed without departing from the novel concepts of the invention. It will be further apparent to those skilled in the art that additional modifications and variations of the above-described illustrative embodiment of the invention may be effected without departing from the spirit and scope of the novel concepts of the invention.

We claim:

1. A compensation method adapted for use in color measuring apparatus for measuring color characteristics of actual object samples under test, said method comprising the steps of:

employing a reference sample and projecting light toward said reference sample through use of a light source means;

performing a first plurality of measurements of said reference sample, with each measurement providing a measured color characteristic value of said reference sample for each of a series of spectral segments across a light spectrum;

said first plurality of measurements of said reference sample includes a second plurality of measurements made over time for each spectral segment of said series of spectral segments;

performing a plurality of side sensor measurements, with each of said side sensor measurements providing a measured light source intensity value indicative of the intensity of said light source means, and with said side sensor measurements being performed in the absence of complete spectral equivalence between said side sensor measurements and said first plurality of measurements of said reference sample;

determining a filter compensation coefficient for each of said segment as a function of a ratio of at least two of said measured color characteristic values of said reference sample for the corresponding segment, and as a function of a ratio of at least two of said measured light source intensity values; and compensating measurements of color characteristic values of said actual object samples under test for a particular segment, as a function at least in part of said filter compensation coefficient for said particular segment.

2. A compensation method in accordance with claim 1 characterized in that said plurality of measurements of said reference sample provides timed-sequence sets of said measured color characteristic values of said reference sample, with each set of said measured color characteristic values comprising a measured color characteristic value for each spectral segment of said series of spectral segments.

3. A compensation method in accordance with claim 2 characterized in that said plurality of side sensor measurements comprises a separate side sensor measurement for each set of said sets of said measured color characteristic values.

4. A compensation method in accordance with claim 1 characterized in that means employed for performing said plurality of side sensor measurements comprises a filter maintained in a stationary position during performance of said plurality of side sensor measurements.

5. A compensation method in accordance with claim 1 characterized in that in determining said filter compensation coefficients, a separate filter compensation coefficient is determined for each of said segments as a function of certain of said measured color characteristic values of said reference sample associated only with that particular segment, and as a function of certain of said measured light source intensity values.

6. A compensation method in accordance with claim 1 characterized in that said measurements of color characteristic values of said actual object samples under test are compensated without requiring matching of spectral response characteristics of means employed for performing said plurality of side sensor measurements with spectral response characteristics of means employed for performing said plurality of measurements of said reference sample.

7. A compensation method in accordance with claim 1, characterized in that each of said plurality of side sensor measurements is performed employing a single side sensor and an associated filter, so that the spectral response characteristic of said side sensor and said associated filter is identical for each of said plurality of side sensor measurements.

8. A compensation method in accordance with claim 7 characterized in that said associated filter is maintained in a stationary position relative to said side sensor during performance of said side sensor measurements.

9. A compensation method in accordance with claim 1 characterized in that said method further comprises prohibiting initiation of performance of said plurality of measurements of said reference sample, and prohibiting initiation of performance of said plurality of side sensor measurements, until a predetermined period of time has elapsed since any prior measurements of said reference sample or prior side sensor measurements.

10. A compensation method in accordance with claim 1 characterized in that each of said filter compensation coefficients is determined in accordance with the following:

$$CCx = ((RS1x/RSNx) - 1)/((SS1/SSN) - 1)$$

where $CCx$ is the filter compensation coefficient for segment x, $RS1x$ is a first measured color characteristic value of said reference sample for segment x, $RSNx$ is a last measured color characteristic value of said reference sample for segment x, $SS1$ is a measured light source intensity value for a first one of said plurality of side sensor measurements, and $SSN$ is a measured light source intensity value for a last one of said plurality of said side sensor measurements.

11. A compensation method in accordance with claim 1 characterized in that said plurality of side sensor measurements correspond in number to said plurality of measurements of said reference sample.

12. A compensation method in accordance with claim 11 characterized in that said plurality of measurements of said reference sample provides timed-sequence sets of said measured color characteristic values of said reference sample, and each of said plurality of side sensor measurements corresponds in time to one of said timed-sequence sets of said measured color characteristic values.

13. A compensation method in accordance with claim 12 characterized in that said timed-sequence sets and said plurality of side sensor measurements are each five in number.

14. A compensation method in accordance with claim 1 characterized in that said plurality of measurements of said reference sample and said plurality of side sensor measurements are performed in a timed sequence.

15. A compensation method in accordance with claim 14 characterized in that the period of time between measurements of each of said timed-sequences is approximately three seconds.

16. A compensation method in accordance with claim 1 characterized in that said series of spectral segments comprises sixteen in number.

17. A compensation method in accordance with claim 1 characterized in that said method further comprises the steps of:

for each of said spectral segments, and for each of said plurality of measurements of said reference sample, determining a normalized color characteristic value as a function of said measured color characteristic value for that particular segment and measurement of said reference sample, and as a function of said filter compensation coefficient for that particular segment and certain of said measured light source intensity values; and compensating said measurements of color characteristic values of actual object samples under test for a particular segment, as a function in part of said normalized color characteristic values.

18. A compensation method in accordance with claim 17 characterized in that each of said normalized color characteristic values is determined in accordance with the following:

$$RScxa = RSxa[(((SS1/SSa)-1)CCx)+1]$$

where RScxa is a normalized color characteristic value for segment x and measurement a, RSxa is a measured color characteristic value of said reference sample for segment x and measurement a, SS1 is a measured light source intensity value for a first one of said plurality of side sensor measurements, SSa is a measured light source intensity value for a current one of said plurality of side sensor measurements, and CCx is a filter compensation coefficient for a current spectral segment.

19. A compensation method in accordance with claim 17 characterized in that said method further comprises the steps of:

determining a scale factor for each of said segments, each of said scale factors representing the conversion of a measured color characteristic quantity to a color characteristic value relative to a desired color characteristic value; and compensating said measurements of color characteristic values of actual object samples under test for a particular segment, as a function in part of said scale factor for said particular segment.

20. A compensation method in accordance with claim 1 characterized in that said method further comprises the step of input or pre-storage of reference data indicative of expected or desired spectral characteristics of said reference sample, for each segment of said series of spectral segments.

21. A compensation method in accordance with claim 20 characterized in that said method further comprises the steps of:

determining a scale factor for each of said segments, in accordance with the following:

$$WSx = [(RSc1x + RSc2x + \ldots RScNx)/N]/WRx$$

where WSx is a scale factor for segment x, RSc1x is a normalized color characteristic value for a first one of said plurality of measurements of said reference sample for segment x, RSc2x is a normalized color characteristic value for a second one of said plurality of measurements of said reference sample for segment x, and RScNx is a normalized color characteristic value for a last one of said plurality of measurements of said reference sample and segment x, and WRx is a desired color characteristic value for segment x; and compensating said measurements of color characteristic values of actual object samples under test for a particular segment, as a function in part of said scale factor for said particular segment.

22. A compensation method in accordance with claim 1 characterized in that said color measuring apparatus is a spectrophotometer, and said measured color characteristic values of said reference sample for each of a series of spectral segments across a light spectrum are indicative of measured reflectance values of light reflected from said reference sample.

23. A compensation method in accordance with claim 1 characterized in that said measurements of color characteristic values of said actual object samples under test are compensated in accordance with the foregoing:

$$Rx = WSx[RSx((CCx((SS1/SS)-1))+1)]$$

where Rx is a compensated measurement of color characteristic values of said object samples under test, WSx represents a scale factor for segment x, RSx represents an actual measured color characteristic value of said object sample under test for segment x, CCx represents one of said filter compensation coefficients for segment x, SS1 is a measured light source intensity value for a first one of said plurality of side sensor measurements, and SS is a current measured light source intensity value.

24. A compensation method in accordance with claim 1 characterized in that said method further comprises the steps of:

determining temperature values of said light source means or area adjacent said light source means; and compensating said measurements of color characteristic values of said actual object samples under test as a function at least in part of said temperature values.

25. A compensation method in accordance with claim 24 characterized in that said method further comprises the steps of:

determining a temperature coefficient for each segment of said series of spectral segments; and compensating measurements of color characteristic values for a particular segment of said actual object samples under test as a function of said temperature coefficient for said particular segment, a then current one of said temperature values and at least one temperature value obtained during performance of said plurality of measurements of said reference sample.

26. A compensation method in accordance with claim 24 characterized in that said method further comprises the steps of:
   determining a temperature coefficient associated specifically with means employed for performing said plurality of side sensor measurements; and
   compensating measurements of color characteristic values of said actual object samples under test as a function of said temperature coefficient, a then current one of said temperature values, and at least one temperature value obtained during performance of said plurality of side sensor measurements.

27. A compensation method adapted for use in color measuring apparatus for measuring color characteristics of actual object samples under test, said method comprising the steps of:
   employing a reference sample and projecting light toward said reference sample through use of a light source means;
   performing a plurality of measurements of said reference sample, with said measurements providing measured color characteristic values of said reference sample for a series of spectral segments across a light spectrum;
   performing a plurality of side sensor measurements, with said side sensor measurements providing measured light source intensity values indicative of the intensity of said light source means;
   determining at least one temperature value of said light source means or area adjacent said light source means during performance of said plurality of measurements of said reference sample;
   determining a temperature coefficient for each segment of said series of spectral segments;
   determining at least one temperature value of said light source means or area adjacent said light source means during performance of measurements of color characteristic values of said actual object samples under test; and
   compensating measurements of color characteristic values for a particular segment of said actual object samples under test as a function at least in part of said temperature coefficient for said particular segment, said at least one temperature value obtained during measurements of color characteristic values of said actual object samples under test, and at least one temperature value obtained during performance of said plurality of measurements of said reference sample.

28. A compensation method adapted for use in color measuring apparatus for measuring color characteristics of actual object samples under test, said method comprising the steps of:
   employing a reference sample and projecting light toward said reference sample through use of a light source means;
   performing a plurality of measurements of said reference sample, with said measurements providing measured color characteristic values of said reference sample for a series of spectral segments across a light spectrum;
   performing a plurality of side sensor measurements, with said side sensor measurements providing measured light source intensity values indicative of the intensity of said light source means;
   determining at least one temperature value of said light source means or area adjacent said light source means during performance of said plurality of measurements of said reference sample;
   determining a temperature coefficient for means employed for performing said plurality of side sensor measurements;
   determining at least one temperature value of said light source means or area adjacent said light source means during performance of measurements of color characteristic values of said actual object samples under test; and
   compensating measurements of color characteristic values of said actual object samples under test as a function at least in part of said temperature coefficient, said at least one temperature value obtained during performance of said plurality of measurements of said reference sample, and said at least one temperature value obtained during performance of said measurements of color characteristic values of said actual object samples under test.

29. A color measuring apparatus for use in measuring color characteristics of actual object samples under test and for compensating measurements of said color characteristics through the use of a reference sample, said apparatus comprising:
   light source means for projecting light toward said reference sample;
   color characteristic measuring means for performing a first plurality of measurements of said reference sample, and for generating signals representative of measured color characteristic values of said reference sample for each of a series of spectral segments across a light spectrum and wherein said first plurality of measurements of said reference sample includes a second plurality of measurements made over time for each spectral segment of said series of spectral segments;
   means for performing a plurality of side sensor measurements and generating signals representative of measured light source intensity values indicative of the intensity of said light source means, and with said side sensor measurements being performed in the absence of complete spectral equivalence between said side sensor measurements and said first plurality of measurements of said reference sample;
   a processor responsive to said signals representative of said measured color characteristic values and responsive to said signals representative of said measured light source intensity values for determining a filter compensation coefficient for each of said segments as a function of a ratio of at least two of said measured color characteristic values of said reference sample for the corresponding segment and as a function of a ratio of at least two of said measured light source intensity values; and
   said processor comprising means for compensating measurements of color characteristic values of said actual object samples under test for a particular segment, as a function at least in part of said filter compensation coefficient for said particular segment.

30. A color measuring apparatus in accordance with claim 29 characterized in that said filter maintained in a stationary position during performance of said plurality of side sensor measurements.

31. A color measuring apparatus in accordance with claim 29 characterized in that each of said plurality of side sensor measurements is performed employing only a single side sensor and an associated filter so that the spectral response characteristic of said single side sensor and said associated filter is identical for each of said plurality of side sensor measurements.

32. A color measuring apparatus in accordance with claim 31 characterized in that said associated filter is maintained in a stationary position relative to said single side sensor during performance of said plurality of side sensor measurements.

33. A color measuring apparatus in accordance with claim 29 characterized in that said apparatus further comprises means for prohibiting initiation of performance of said plurality of measurements of said reference sample, and prohibiting initiation of performance of said plurality of side sensor measurements, until a predetermined period of time has elapsed since any prior measurements of said reference sample or prior side sensor measurements.

34. A color measuring apparatus in accordance with claim 29 characterized in that said processor further comprises means, for each of said spectral segments and for each of said plurality of measurements of said reference sample, for determining a normalized color characteristic value as a function of said measured color characteristic value for that particular segment and measurement of said reference sample, and as a function of said filter compensation coefficient for that particular segment and certain of said measured light source intensity values; and said means for compensating said measurements of color characteristic values of actual object samples under test further comprises means for compensating said measurements of color characteristic values of object samples under test for a particular segment as a function in part of said normalized color characteristic values.

35. A color measuring apparatus in accordance with claim 34 characterized in that said processor further comprises:

means for determining a scale factor for each of said segments, each of said scale factors representing the conversion of a measured color characteristic quantity to a color characteristic value relative to a desired color characteristic value; and means for compensating said measurements of color characteristic values of actual object samples under test for a particular segment, as a function in part of said scale factor for said particular segment.

36. A color measuring apparatus in accordance with claim 29 characterized in that said apparatus further comprises means for inputting reference data indicative of expected or desired spectral characteristics of said reference sample, for each segment of said series of spectral segments.

37. A color measuring apparatus in accordance with claim 29 characterized in that said apparatus further comprises means for storing reference data indicative of expected or desired spectral characteristics of said reference sample, for each segment of said series of spectral segments.

38. A color measuring apparatus in accordance with claim 29 characterized in that said apparatus is a spectrophotometer, and said measured color characteristic values of said reference sample for each segment of a series of spectral segments across a light spectrum are indicative of measured reflectance values of light reflected from said reference sample.

39. A color measuring apparatus in accordance with claim 29 characterized in that said apparatus further comprises:

means for determining temperature values of said light source means or area adjacent said light source means; and means for compensating said measurements of color characteristic values of said actual object samples under test as a function at least in part of said temperature values.

40. A color measuring apparatus in accordance with claim 39 characterized in that said apparatus further comprises:

means for determining a temperature coefficient for each segment of said series of spectral segments; and means for compensating measurements of color characteristic values for a particular segment of said actual object samples under test as a function of said temperature coefficient for said particular segment, a then current one of said temperature values and at least one temperature value obtained during performance of said plurality of measurements of said reference sample.

41. A color measuring apparatus in accordance with claim 39 characterized in that said apparatus further comprises:

means for determining a temperature coefficient associated specifically with said means for performing said plurality of side sensor measurements; and means for compensating measurements of color characteristic values of said actual object samples under test as a function of said temperature coefficient, a then current one of said temperature values, and at least one temperature value obtained during performance of said plurality of side sensor measurements.

42. A color measuring apparatus for use in measuring color characteristics of actual object samples under test and for compensating measurements of said color characteristics through the use of a reference sample, said apparatus comprising:

light source means for projecting light toward said reference sample;

color characteristic measuring means for performing a plurality of measurement of said reference sample, and for generating signals representative of measured color characteristic values of said reference sample for a series of spectral segments across a light spectrum;

means for performing a plurality of side sensor measurements and generating signals representative of measured light source intensity values indicative of the intensity of said light source means;

means for determining at least one temperature value of said light source means or area adjacent said light source means during performance of said plurality of measurements of said reference sample;

means for determining a temperature coefficient for each segment of said series of spectral segments;

means for determining at least one temperature value of said light source means or area adjacent said light source means during performance of measurements of color characteristic values of said actual object samples under test; and means for compensating measurements of color characteristic values for a particular segment of said actual object samples under test as a function at least in part of said temperature coefficient for said particular segment, said at least one temperature value obtained during measurements of color characteristic values of said actual object samples under test, and at least one temperature value obtained during performance of said plurality of measurements of said reference sample.

43. A color measuring apparatus for measuring color characteristics of actual object samples under test and for compensating measurements of said color characteristics through the use of a reference sample, said apparatus comprising:

light source means for projecting light toward said reference sample;

means for performing a plurality of measurements of said reference sample, and for generating signals representative of measured color characteristic values of said reference sample for a series of spectral segments across a light spectrum;

means for performing a plurality of side sensor measurements and for generating signals representative of measured light source intensity values indicative of the intensity of said light source means;

means for determining at least one temperature value of said light source means or area adjacent said light source means during performance of said plurality of measurements of said reference sample;

means for determining a temperature coefficient for said means for performing said plurality of side sensor measurements;

means for determining at least one temperature value of said light source means or area adjacent said light source means during performance of measurements of color characteristic values of said actual object samples under test; and means for compensating measurements of color characteristic values of said actual object samples under test as a function at least in part of said temperature coefficient, said at least one temperature value obtained during performance of said plurality of measurements of said reference sample, and said at least one temperature value obtained during performance of said measurements of color characteristic values of said actual object samples under test.

* * * * *